(12) United States Patent
Vecchio et al.

(10) Patent No.: US 10,780,294 B2
(45) Date of Patent: Sep. 22, 2020

(54) SYSTEM AND METHOD FOR PHOTO-DYNAMIC PROCEDURE

(71) Applicant: The General Hospital Corporation, Boston, MA (US)

(72) Inventors: Daniela Vecchio, Cambridge, MA (US); Michael R. Hamblin, Boston, MA (US); Yingying Huang, Boston, MA (US); Liyi Huang, Boston, MA (US); Giacomo Landi, Cambridge, MA (US); Jeffrey Gelfand, Boston, MA (US); Timothy Brauns, Boston, MA (US)

(73) Assignee: The General Hospital Corporation, Boston, MA (US)

(*) Notice: Subject to any disclaimer, the term of this patent is extended or adjusted under 35 U.S.C. 154(b) by 72 days.

(21) Appl. No.: 15/528,015
(22) PCT Filed: Nov. 18, 2015
(86) PCT No.: PCT/US2015/061328
§ 371 (c)(1),
(2) Date: May 18, 2017
(87) PCT Pub. No.: WO2016/081594
PCT Pub. Date: May 26, 2016

(65) Prior Publication Data
US 2018/0036552 A1 Feb. 8, 2018

Related U.S. Application Data

(60) Provisional application No. 62/081,636, filed on Nov. 19, 2014.

(51) Int. Cl.
*A61N 5/06* (2006.01)
*A61K 41/00* (2020.01)
(Continued)

(52) U.S. Cl.
CPC ............ *A61N 5/062* (2013.01); *A61B 18/24* (2013.01); *A61K 31/045* (2013.01); *A61K 31/43* (2013.01);
(Continued)

(58) Field of Classification Search
CPC .............................. A61K 41/0057; A61N 5/062
See application file for complete search history.

(56) References Cited

U.S. PATENT DOCUMENTS

| 5,250,045 A | 10/1993 | Bohley |
| 5,797,868 A | 8/1998 | Leone |

(Continued)

FOREIGN PATENT DOCUMENTS

| WO | WO 20090131548 A1 | 10/2009 |
| WO | WO 20130177043 A1 | 11/2013 |

OTHER PUBLICATIONS

Huang et al, Paradoxical potentiation of methylene blue-mediated antimicrobial photodynamic inactivation by sodium azide: Role of ambient oxygen and azide radicals, Free Radic Biol Med, Dec. 1, 2012, vol. 53 (11): 2062-2071). (Year: 2012).*

International Search report and Written Opinion for International Application No. PCT/US2015/061328 dated Jan. 29, 2016, 10 pages.

Huang et al., Paradoxical potentiation of methylene blue-mediated antimicrobial photodynamic inactivation by sodium azide: Role of ambiant oxygen and azide radicals, Free Radic Biol Med, Dec. 1, 2012, vol. 53 (11): 2062-2071.

(Continued)

*Primary Examiner* — Laura A Bouchelle
(74) *Attorney, Agent, or Firm* — Quarles & Brady LLP; Yakov Sidorin

(57) ABSTRACT

A problem of incomplete inhibition of harmful cells/bacteria and short duration of time, after the photodynamic treatment, during which such cells may re-grow, is solved by exposing the target bacteria with a multi-component photosensitizer material formed by adding a predetermined potentiating chemical to a conventional single-component photosensitizer at the target, prior to irradiating the target with light. The multi-component photosensitizer is effectuated by forming a mix of the two chemical compositions or by (Continued)

sequential exposure of the bacteria to a single-component photosensitizer and the potentiating chemical of choice.

8 Claims, 17 Drawing Sheets

(51) Int. Cl.
*A61K 41/17* (2020.01)
*A61B 18/24* (2006.01)
*A61K 31/045* (2006.01)
*A61K 31/43* (2006.01)
*G02B 23/26* (2006.01)

(52) U.S. Cl.
CPC .......... *A61K 41/0057* (2013.01); *A61K 41/17* (2020.01); *A61N 5/0624* (2013.01); *G02B 23/26* (2013.01)

(56) References Cited

U.S. PATENT DOCUMENTS

2007/0059316 A1\* 3/2007 Pallenberg ......... A61K 41/0057
424/178.1
2008/0214518 A1 9/2008 Remmal
2012/0265120 A1\* 10/2012 Beisang, III ......... A61N 5/0624
604/20

OTHER PUBLICATIONS

Denis et al., Thiocyanate potentiates antimicrobial photodynamic therapy: In situ generation of the sulfur trioxide radical anion by singlet oxygen, Free Radical Biology and Medicine 65 (2013) 800-810.

\* cited by examiner

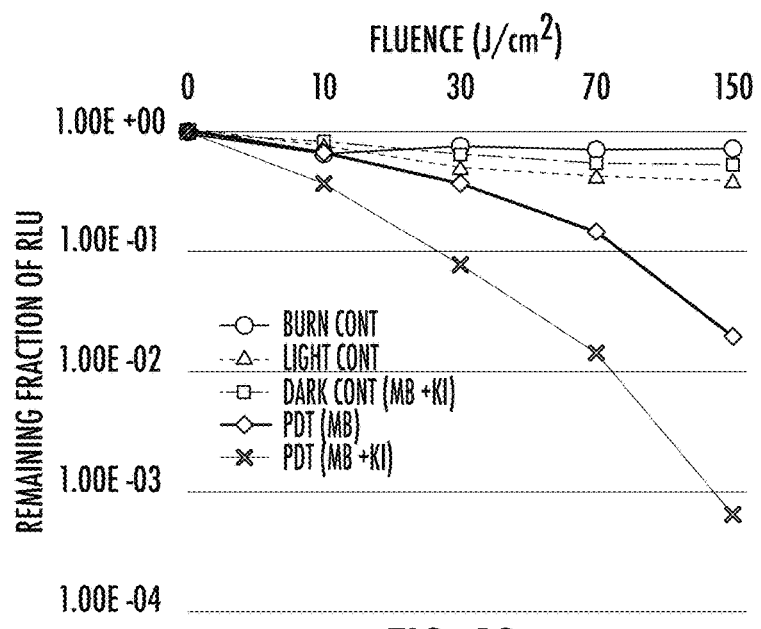
FIG. 18
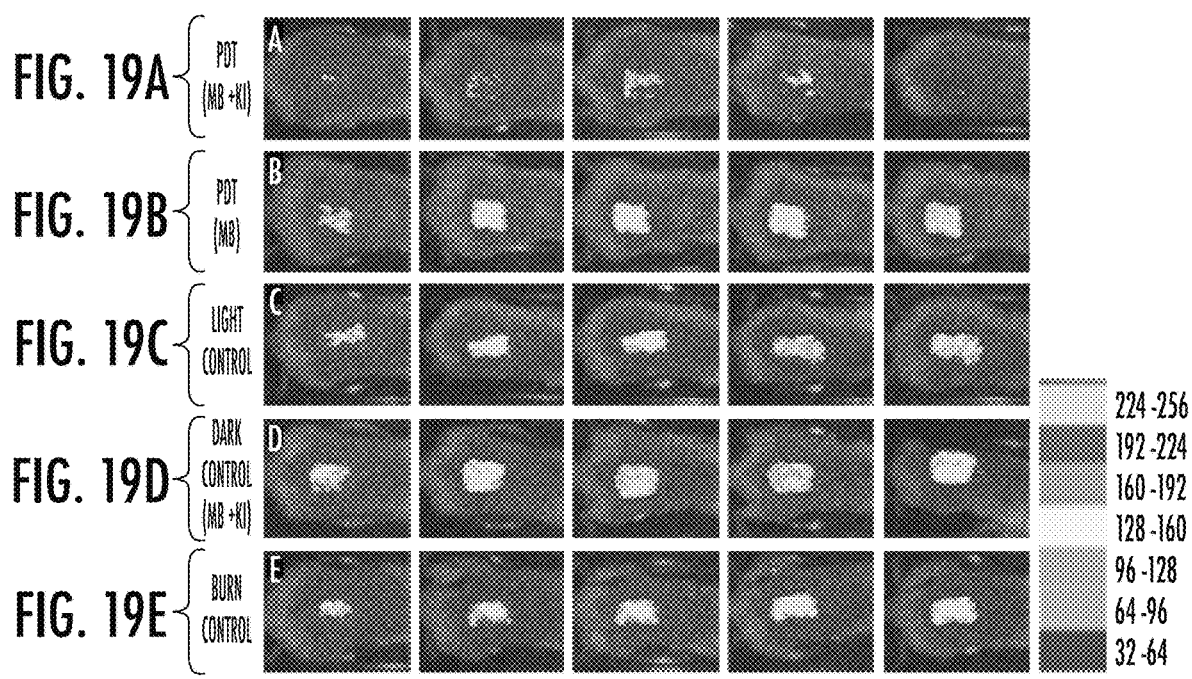

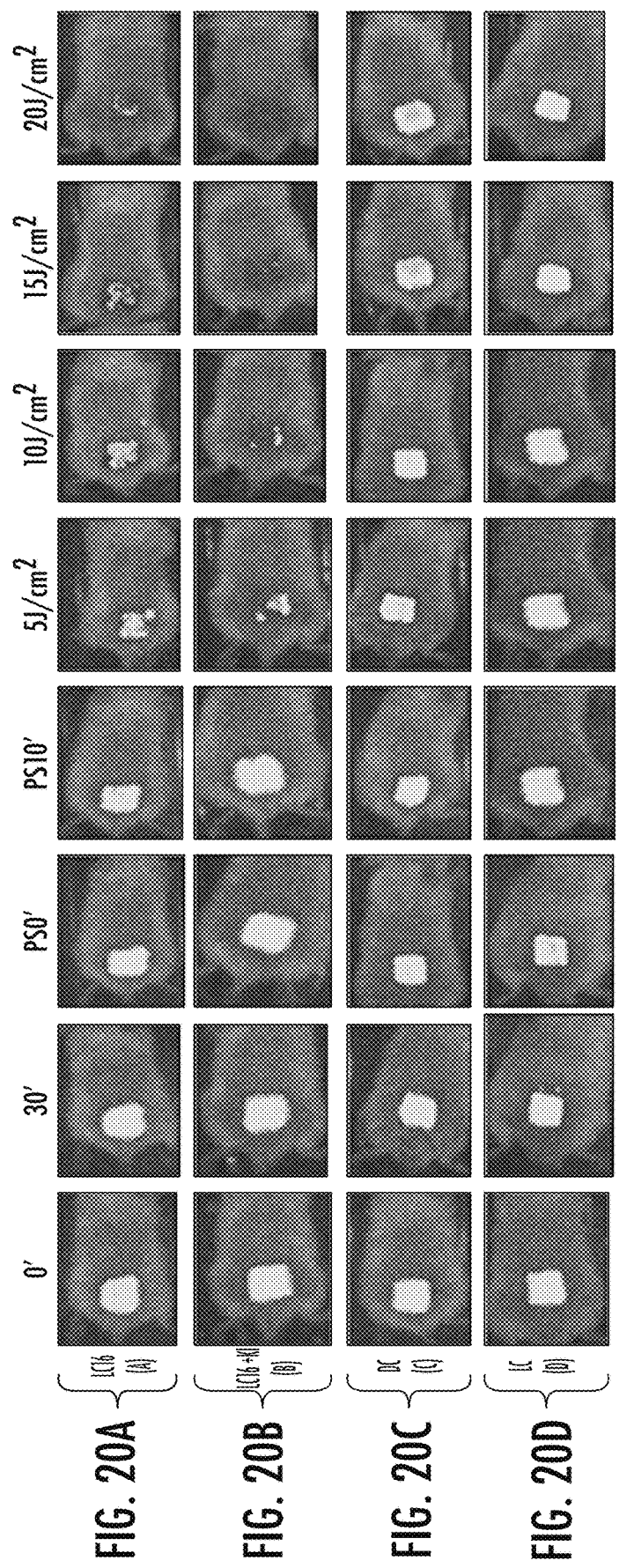

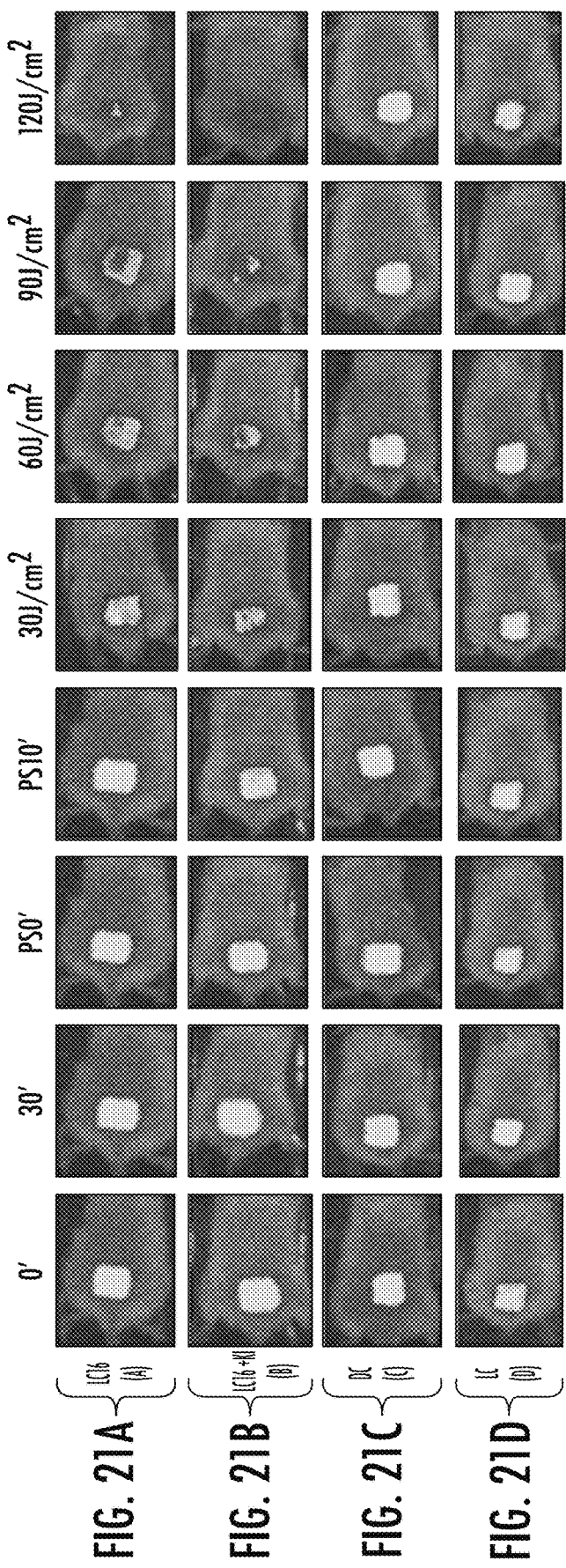

SYSTEM AND METHOD FOR PHOTO-DYNAMIC PROCEDURE

CROSS-REFERENCE TO RELATED APPLICATIONS

The present application represents the U.S. National Stage of International Application No. PCT/US2015/061328, filed Nov. 18, 2015, which claims priority from the U.S. Provisional Patent Application No. 62/081,636 filed on Nov. 19, 2014 and titled "System and Method for Photo-Dynamic Procedure"; the disclosure of each of the above-identified patent documents is incorporated herein by reference.

TECHNICAL FIELD

This invention is related to systems and methods utilizing species producing antimicrobial effects and, in particular, to increase of efficiency of a process of photodynamic inactivation of target bacteria mediated by a single-component photosensitizer with the use of a pre-determined potentiating composition of matter.

BACKGROUND

The ever-growing spread of resistance of microbes to antibiotics urges the search for antimicrobial methodologies to which microbes may be unable to develop resistance. Photodynamic inactivation (PDI) is an alternative approach to kill multidrug-resistant microorganisms with the use of the combination of a single-component non-toxic material (termed a photosensitizer, or PS) and harmless visible light. Conventionally, the PDI process employs a PS in the form of a single-component non-toxic dye together with irradiation of such PS with low intensity visible light. In the presence of oxygen, light induces the formation of reactive oxidative species (ROS), which are generated by energy- or electron transfer from the PS long-lived triplet excited state that are able to oxidize biomolecules and thereby kill microbial cells.

The photochemistry from the PS triplet state can occur by two parallel pathways: Type 1 involves electron transfer to oxygen initially forming superoxide and eventual production of cytotoxic hydroxyl radicals; while Type 2 involves energy transfer to ground state oxygen and production of cytotoxic singlet oxygen. It is known that selectivity of the PS for bacteria over host medium can be obtained by the appropriate chemical design to ensure that the PS molecule preferentially binds to the bacterial cells.

Although various advances in chemical design of new PS's have been made, the dye-based PS's have some practical limitations leading to recurrence and/or regeneration of harmful bacteria after the irradiation of the PS has been completed. The thus-far attempted chemical enhancement(s) of the conventionally-used methylene blue (MB) remained impractical due to the toxicity of the resulting compound(s).

SUMMARY

Embodiments of the invention provide a method for photodynamic inactivation of target bacteria. The method includes a step of treating the target bacteria to form a first amount of treated bacteria by establishing contact between first and second compositions of matter and the target bacteria. The first composition of matter includes a single-component photosensitizer (PS) having a first efficiency in mediating the process on its own, while the second composition of matter has no efficiency in mediating the process on its own. Generally, the step of treating includes establishing contact between the target bacteria and the first composition of matter including one of methylene blue, toluidine blue, new methylene blue, dimethyl-methylene blue, Nile blue derivative material, fullerene, and titania, and establishing contact between the living bacteria and the second composition of matter including at least one of an iodide salt of an alkaline metal, a nitrite salt of an alkaline metal, a thiocyanate salt of an alkaline metal, a selenocyanate sale of an alkaline metal, and a bromide salt of an alkaline metal.

The method further includes a step of irradiating the first amount of treated bacteria, for a pre-determined duration of time, with light having a chosen wavelength to reduce the first amount of treated bacteria. The chosen wavelength is determined such that light at the chosen wavelength triggers the process of photodynamic inactivation when the target bacteria has been treated with only the single-component PS. The method may further include intermixing the first and second compositions of matter prior to the step of treating the living bacteria and, in a specific case, intermixing a first solution of the first composition of matter and a second solution of the second composition of matter. Solutions may be aqueous solutions.

The step of treating, in one implementation, includes sequentially applying the first and second compositions of matter to the living bacteria, and can be implemented when the first composition of matter is already carried by a support surface. As a result of such sequential application, the first amount is reduced by a factor of K>L; here, L is a factor of reduction of a second amount of treated bacteria as a result of irradiating a second amount of treated bacteria with said light for said pre-determined duration of time, and the second amount of treated bacteria is an amount formed as a result of establishing contact between a mixture of the first and second compositions of matter and said target bacteria.

For example, the step of treating includes establishing contact between the first and second compositions of matter and the target bacteria carried by a surface of at least one of a dental tool (such as a dental implant or a titanium dioxide nanotubes incorporated into a filling for teeth, for example), a surgical tool, and a surface in a clinical environment. In one embodiment, the step of irradiating includes reducing the first amount of treated bacteria by a factor of M>N. Here, N is a factor of reduction of a second amount of treated bacteria as a result of irradiating a second amount of treated bacteria with the same light for the same pre-determined duration of time, while the second amount of treated bacteria is an amount formed as a result of establishing contact between only the first composition of matter and the target bacteria. M/N is at least 10; preferably at least 100; More preferably at least 1,000; and even more preferably, at least 10,000.

In a related embodiment, the step of treating includes transporting at least one of the first and second compositions of matter along a delivery channel of a catheter to a distal portion of the catheter, while the step of irradiating includes transmitting such light along a body of the catheter and, in particular, in an optical waveguide disposed within a wall of the catheter to the treated bacteria disposed near the distal portion of the catheter.

BRIEF DESCRIPTION OF DRAWINGS

The invention will be more fully understood by referring to the following Detailed Description of Specific Embodiments in conjunction with the generally not-to-scale Drawings, of which:

(FIGS. 6B, 6D);

FIG. 11A: $TiO_2$ 1 mM on MRSA (10(8) cells/mL); FIG. 11B: $TiO_2$ 5 mM on MRSA (10(8) cells/mL); FIG. 11C: $TiO_2$ 1 mM on *E. coli* (10(8) cells/mL); FIG. 11D: $TiO_2$ 5 mM on *E. coli* (10(8) cells/mL); FIG. 11E: $TiO_2$ 5 mM on *C. albicans* (10(7) cells/mL). Values are means of 3 repetitions and bars are SD.

FIG. 13A: SOSG; FIG. 13B: HPF. Values are means of 6 wells and bars are SD.

FIG. 14A: absorbance of $I_2$ at 350 nM; FIG. 14B: absorbance spectrum of $I_2$. Values are means of 3 repetitions and bars are SD:

FIG. 18 provides the light-dose-response curves for all groups of FIGS. 17A through 17E;

FIGS. 19A, 19B, 19C, 19D, 19E, 19F, 19G illustrate the results of the follow-up monitoring of burns of FIGS. 17A through 17E after the PDT procedure was concluded;

FIGS. 20A, 20B, 20C, 20D are illustrations of complete elimination of the bioluminescence signal as a result of PDI-treatment of a biological tissue with UVA light, mediated with a combination of LC16 and KI;

FIGS. 21A, 21B, 21C, 21D are illustrations of complete elimination of the bioluminescence signal as a result of PDI-treatment of a biological tissue with white light, mediated with a combination of LC16 and KI;

DETAILED DESCRIPTION

Figure 1A:
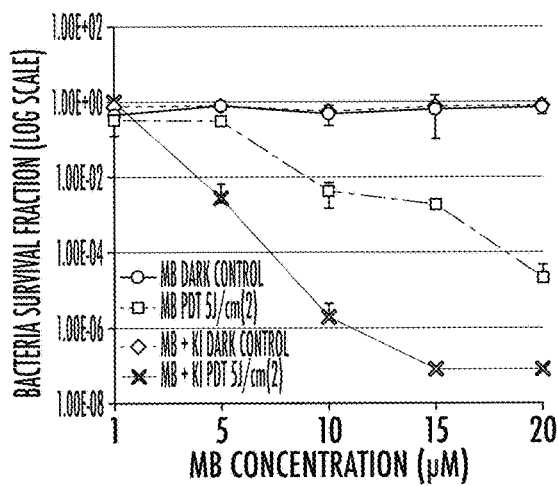
FIGS. 1A, 1B, 1C present plots illustrating results of potentiation of MB-antibacterial PDI by addition of potassium iodide, in vitro, with respect to *S. aureus*.

The idea of the invention stems from the realization that both a photodynamic potency of the PDI of the harmful cells at the target and the duration of time during which, after the PDI treatment, the bacteria does not reappear can be significantly increased (as compared with that of a conventional PDI process) by utilizing either (i) a treatment of the target with a complex, multi-component PS (that includes a practical combination, or aggregation of chosen chemical(s) intermixed with a known single-component PS, in a judiciously predetermined ratio) or (ii) a sequential treatment of the target with the components of a pre-determined multi-component PS (that is, a sequential treatment of the target with a known single-component PS and the chosen chemical (s)).

The problems of practically incomplete effects produced by a conventional PDI process—specifically, incomplete inhibition of harmful cells/bacteria and short duration of time, after the PDI treatment, during which such cells may re-grow—are solved by judiciously treating the target living bacteria with a multi-component PS material (referred to hereinafter as MCPPS) that is formed by operationally adding a predetermined potentiating chemical to a conventional, single-component PS at the target, prior to applying light that initiates photochemistry required for the PDI process to take effect. The addition of the potentiating chemical component to the single-component PS can be effectuated by forming a mix of these two chemical compositions (with which mix the target living bacteria is then treated) or by sequentially treating the bacteria with a single-component PS and the potentiating chemical of choice.

The potentiating chemicals are specifically defined such that, when the MCPPS combination material is irradiated with light at wavelengths tailored to activate the single-component PS in the MCPPS material, the MCPPS material generates reactive inorganic radicals (in a specific case—through Type 1 electron transfer, for example), while in absence of triggering light the generation of such radicals remains substantially non-existent. Furthermore, the MCPPS is designed such that—in stark contradistinction with at least single-component PS's of related art—it is not only non-toxic but, when used for strengthening and increasing the efficiency of the PDI process, prevents recurrence/ regeneration of biological species targeted in the PDI process. In addition, the component of the MCPPS are formulated such as to cause the PDI process to be selective, in that only the targeted biological species are affected and not the ambient environment hosting these species.

Non-limiting examples of the components of the MCPPS formulated according to the idea of the invention include those shown in Table 1.

TABLE 1

| Single-component PS | Wavelength of Activating Light | Potentiating Chemical |
|---|---|---|
| Methylene blue (MB) | 660 nm | Iodide salt (such as, e.g., KI, Nap |
| Toluidine blue (TB) | 630 nm | Nitrite salt (such as, e.g., $KNO_2$, $NaNO_2$) |
| New methylene blue (NMB) | 660 nm | Thiocyanate salt (such as, e.g., KSCN, NaSCN) |
| Dimethyl-methylene blue (DMB) | 630 nm | Selenocyanate salt (such as, e.g., KSeCN, NaSeCN) |
| Nile blue derivative (EtNBS) | 660 nm | Bromide salt (KBr, NaBr) |

Some additional, non-limiting types of a conventional, single-component PS that are potentiated according to the idea of the invention include Azure A (activated at about 650 nm), Azure AB (activated at about 640 nm), Azure C (activated at about 630 nm), thionin (activated at about 600 nm), Riboflavin (activated at 360 nm, 440 nm), titanium dioxide (referred to as titania, activated at 360 nm), copper phthalocyhanine (activated at 670 nm), cationic fullerenes (activated at 360 nm, 415 nm, or with broadband/white light).

According to the idea of the invention, the target living bacteria can be treated with an MCPPS that is formed by combining of any of the single-component PS materials listed in Table 1 or mentioned right after with any of the potentiating chemical listed in Table 1.

For example, combinations of MCPPS-components include: MB and an iodide (or nitrite, or thiocyanate, or selenocyanate, or bromide) salt of alkaline metal; TB and an iodide (or nitrite, or thiocyanate, or selenocyanate, or bromide) salt of alkaline metal; NMB and an iodide (or nitrite, or thiocyanate, or selenocyanate, or bromide) salt of alkaline metal; DMB and an iodide (or nitrite, or thiocyanate, or selenocyanate, or bromide) salt of alkaline metal; EtNBS and an iodide (or nitrite, or thiocyanate, or selenocyanate, or bromide) salt of alkaline metal; titanium dioxide and an iodide (or nitrite, or thiocyanate, or selenocyanate, or bromide) salt of alkaline metal; cationic fullerenes and an iodide (or nitrite, or thiocyanate, or selenocyanate, or bromide) salt of alkaline metal.

The following examples illustrate empirical proof of operational advantages of a method of the invention acquired in but several, non-limiting experiments.

Example 1: Formation of MCPPS from Methylene Blue and Salt of Alkaline Metal

While the following discussion below is presented in specific reference to KI and methylene blue (MB), it is understood that similar results are obtained with the use of harmless and intert salts such as iodides, nitrites, thiocyanates, selenocyanates and bromides, to name just a few for potentiation of various other single-components PS.

Methylene blue (MB), a phenothiazinium dye, is probably the most commonly studied antimicrobial PS. Several studies have reported its activity in vitro, and in animal models of infection, and MB has received regulatory approval to mediate photodynamic therapy (PDT) of dental infectious diseases such as periodontitis and caries, and is under clinical investigation for nasal decontamination and chronic sinusitis in some countries. MB is well known to act by both the type 1 mechanism (producing reactive oxygen species including hydroxyl radicals) and by the type 2 mechanism (producing singlet oxygen), although singlet oxygen is more often credited with being the most effective antimicrobial species produced during PDT.

According to the idea of the invention, an MCPPS was created by potentiating the MB-mediated PDI bacteria inactivation with the addition of KI. The increase of efficiency of bacteria inactivation with such MCPPS as compared to the MB alone was empirically demonstrated against S. aureus, and E. coli using different concentrations of MB with a constant concentration of KI and also the opposite (using different concentrations of KI with a constant concentration of MB).

Materials.

1) Methylene blue (MB), potassium iodide (KI), Lugol's solution and all other reagents, were purchased from Sigma-Aldrich (St. Louis, Mo.) unless indicated. MB stock solution was prepared in $dH_2O$ and stored at 4° C. in the dark for no more than 24 hrs prior to use. KI solution was prepared in $dH_2O$ as required immediately before experimentation. The singlet oxygen sensor green (SOSG) and hydroxyphenyl fluorescein (HPF) probes to detect singlet oxygen or hydroxyl radicals were purchased from Life Technologies (Grand Island, N.Y., USA).

2) Staphylococcus aureus (NCTC 8325) and Escherichia coli K12 (ATCC 33780) were chosen as representative Gram (+) and Gram (−) bacteria respectively, for in vitro studies. A colony of bacteria was suspended in 25 ml of brain heart infusion (BHI) broth (Becton, Dickinson, and Company, Franklin Lakes, N.J.) and grown overnight in a shaker incubator (New Brunswick Scientific, Edison, N.J.) at 120 rpm in aerobic condition at 37° C. An aliquot of 1 ml from overnight suspension was refreshed in fresh BHI for 2 hours at 37° C. to mid-log phase. Cell concentration was estimated by measuring the optical density (OD) at 600 nm [OD of $0.8=10^8$ colony forming units (CFU) cells/mL]. Bacterial suspension was centrifuged, washed and re-suspended in PBS to arrest microbial growth, and used ($10^8$ CFU) for the in vitro or in vivo experiments.

Experiments with MCPPS Containing a Mix of Solutions of the Single-Component PS and Inert Salt.

Figure 2A:
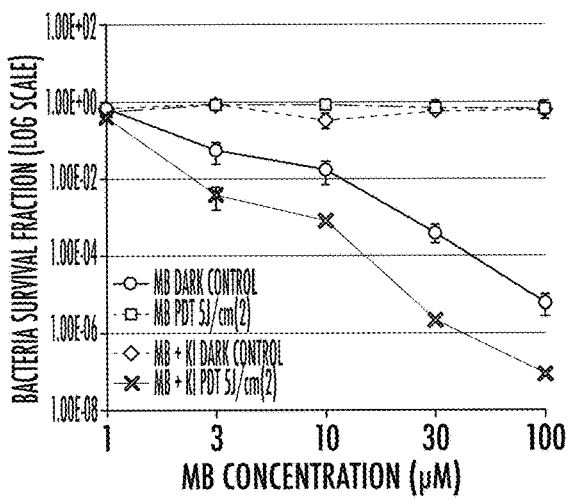
FIGS. 2A, 2B, 2C present plots illustrating results of potentiation of MB-antibacterial PDI by addition of potassium iodide, in vitro, with respect to *E. coli*.

In vitro PDI studies were carried with S. aureus and with E. coli. Cells ($10^8$ CFU; 500 μL) were incubated with different concentrations of MB (0-50 μM) for 15 minutes with either addition or not of 10 mM KI. An aliquot of 100 ul was used as dark control from each sample, another (100 ul) was irradiated with 5 J/$cm^2$ dose of light (660 nm light) and then placed in a new 96 well plate. The aliquots were serially diluted 10-fold in PBS to give dilutions of $10^1$ to $10^5$ times in addition to the original concentration. From each dilution 10 microleter aliquots were seeded horizontally on BHI agar. Plates were streaked in triplicate and incubated for 14-18 hours at 37° C. in the dark to allow the growth of colonies. Each experiment was performed at least three times. Results reported in FIGS. 1A and 2A respectively show the survival fraction curves obtained against the Gram (+) bacterium S. aureus and or Gram (−) bacterium E. coli, incubated for 20 minutes with a range 0-100 μM of MB for both strains with and without addition of 10 mM KI. The addition of KI produced an increase in bacterial killing of 4 and 2 logs for *S. aureus* and *E. coli* respectively.

Figure 1B:
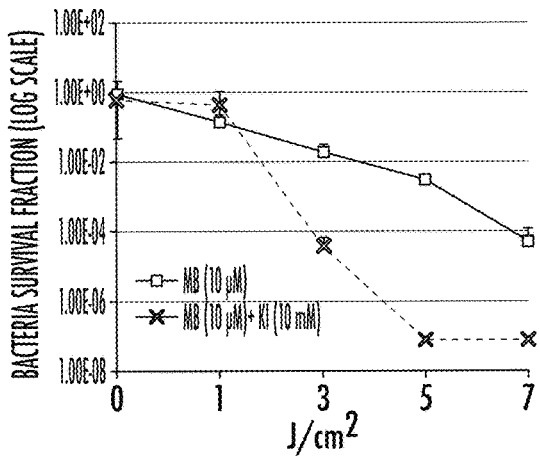
Figure 2B:
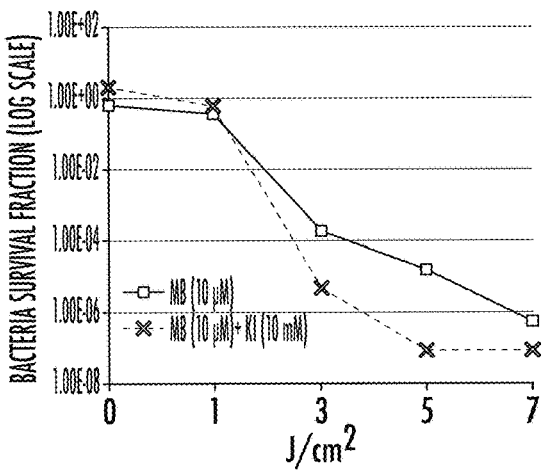

To verify if the bacterial inactivation was also dependent on the light dose, the cells were treated with a single concentration of MB (10 µM) and KI (10 mM) and we irradiated with a range of doses of light (0-7 J/cm$^2$). After treatment, an aliquot from each group of treatment was placed in a new 96-well plate and serial dilution was performed as described above. FIGS. 1B and 2B verify the light-dependent photochemical process in the bacterial killing, by presenting the survival fraction curves obtained against *S. aureus* and *E. coli* incubated for 20 minutes with 10 µM MB for both strains with and without 10 mM KI and delivering increasing doses of light (0-7 J/cm$^2$). In these experiments, with addition of KI, an increase in bacterial killing for both strains was observed. The increase in both experiments was more pronounced in *S. aureus* than *E. coli*.

Figure 1C:
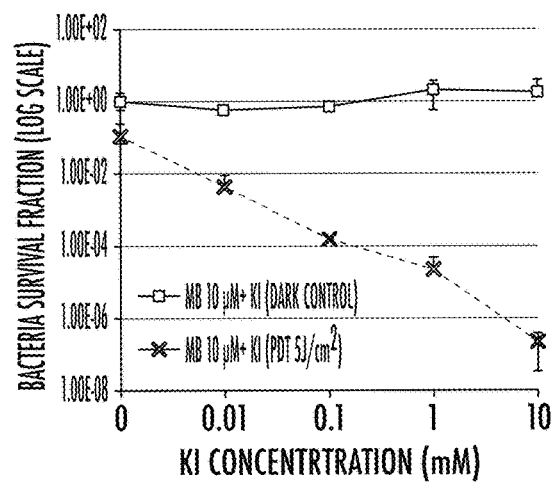
Figure 2C:
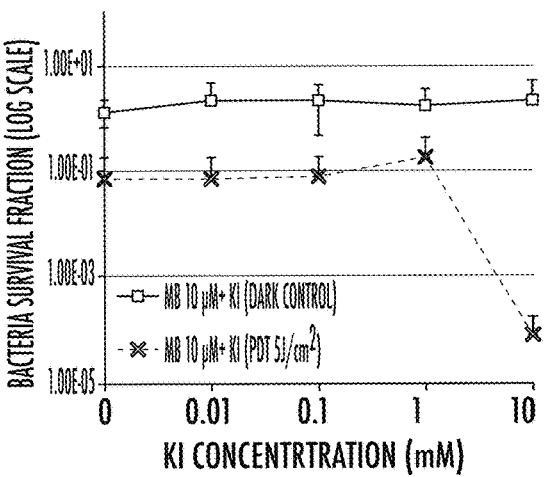

Finally, to investigate the dependency of bacteria inactivation by KI concentration the same experiment were performed using 10 µM MB and adding KI (in the range of concentrations between 0 and 10 mM) just before irradiating the so-treated bacteria with 5 J/cm$^2$ of red light at the wavelengths in the red portion of the optical spectrum (such as 660 nm, for example). FIGS. 1C and 2C present results demonstrating a dose-dependent increase of bacteria killing in *S. aureus* starting from 0.01 mM KI while the enhancement of *E. coli* killing is only observed with 5 mM KI.

A key parameter in PDI was also investigated. The binding of PS to the cell membrane or the uptake of PS into the cells obtained during incubation with MB is a critical point in PDI. For this reason we verified the bacteria killing in presence or not of KI with and without washing the cells with PBS after MB incubation and before adding KI to *S. aureus* and *E. coli* (data not shown). Cells were then either exposed (light) or not (dark) to a range of light doses 0-5 J/cm$^2$ at an irradiance of 100 mW/cm$^2$. For the dark control (DC) we incorporated the time of light exposure. Cells were then serially diluted and plated to count CFU. Survival fractions showed an enhancement of bacteria killing in presence of KI was observed in both strains without a wash while no killing was observed after washing of the MB solution from the cells. The presence of unbound MB in the solution is therefore critical in our experimental conditions. The lack of killing without light in all experimental conditions showed that neither the MB alone nor MB plus KI displayed any appreciable dark toxicity. On the basis of these results we concluded that the presence of KI could increase bacteria killing depending on the doses of MB, light and KI concentration. Moreover the binding of MB to the cell membrane is not involved in the increase in bacterial inactivation.

Figure 3A:
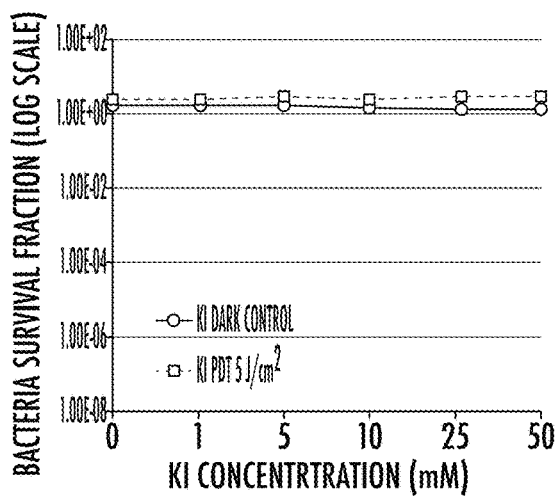
FIGS. 3A, 3B, 3C are plots illustrating effect of potassium iodide alone on bacteria and ma cells in vitro.
Figure 3B:
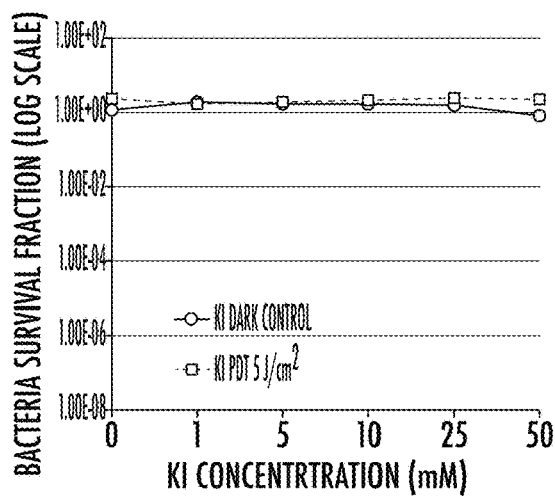
Figure 3C:
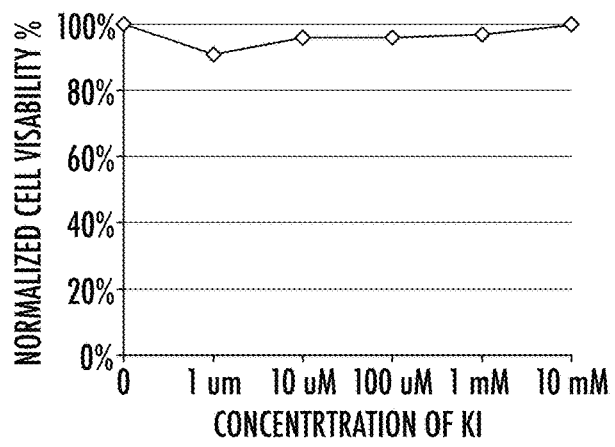

Since there existed a possibility that KI itself could exert an antimicrobial effect, to eliminate or at least account for the direct influence of the KI on the bacteria and to ensure that the final efficiency of the PDI process is attributed to the potentiation of the MB with the KI, additional qualitative performance evaluation tests were performed. Specifically, the bacteria cells (10$^8$ CFU; 500 uL) were incubated with different concentrations of KI (0-50 mM) for 10 minutes in order to verify the toxicity of KI. An aliquot of 100 µl from each sample, was used as dark control, another (100 µl) was irradiated with 5 J/cm$^2$ dose of light (660 nm light) and then placed in a new 96 well plate. The aliquots were serially diluted as before. The results presented in FIGS. 2A, 2B (for *S, aureus* and *E. Coli*) verified that KI itself was not responsible for the increased potency of the PDI treatment observed in the experiments with the MCPPS. In particular, after 10 minutes incubation no bacteria killing was found both in DC and after shining 5 J/cm$^2$ dose of red light. To ensure that KI does not have any side effect in in vivo experiments, the effect of KI in vitro on mammalian dermal skin fibroblasts was performed as well. As shown in FIG. 3C, KI did not kill mammalian cells exposed for 3 hours to the range of KI concentration (0.001-10 mM).

It is concluded, therefore, that the effect observed in bacteria killing potentiation is due to the synergistic effect of the PDI process performed when the bacteria are treated with the MCPPS combining the MB and KI together.

In practice, therefore, an embodiment of the invention is implemented by, initially, treating living bacteria to form a first amount of treated bacteria via establishing contact between pre-mixed (for example, in the form of pre-mixed solutions) first and second compositions of matter and the living bacteria. Here, the first composition of matter comprises a single-component photosensitizer PS having a first efficiency in mediating said process on its own, and the second composition of matter has no efficiency in mediating said process on its own.

The innovation offered by adding a potentiating salt—for example, KI—to a single-component PS solution stems from the fact that by interaction of the ROS and KI during light exposure, the bacterial killing was improved. One mechanism may turn on generation of biocidal molecular iodine ($I_2$ and/or $I_3^-$) or hypoiodite (HOI). Alternatively reactive iodide radicals ($I^\cdot$ or $I_2^{\cdot-}$) could be formed by interaction of the PS excited state with KI that would increase the damage to bacterial cell wall constituents.

Fluorescence Probe Experiments.

Figure 4A:
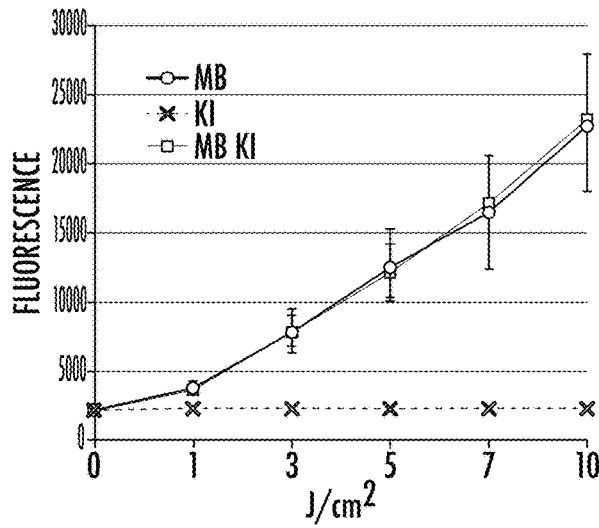
FIGS. 4A, 4B are plots showing the results of fluorescence probe experiments.
Figure 4B:
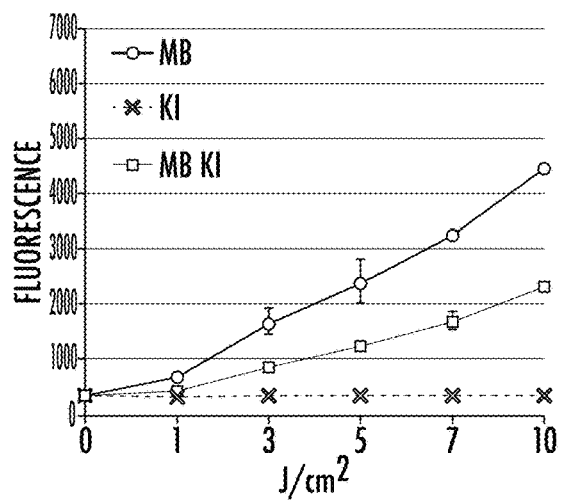

Additional experiments were performed with the use of fluorescent probes—in particular SOSG as a marker of singlet oxygen and HPF as a marker for hydroxyl radical generation—to clarify the mechanisms involved in the effect observed on bacteria killing, we used fluorescent probes. Fluorescent probe experiments were performed in ninety-six-well black-sided plates. Final concentration of 10 µM SOSG or was added to 5 µM MB solution with and without addition of KI in 100 µL PBS per well. Fluorescence spectrometry (SpectraMax M5 plate reader, Molecular Devices, Sunnyvale, Calif.) used excitation and emission at 504 nm and 525 nm for SOSG and 490 nm and 515 nm for HPF, respectively. A range of light doses (0-10 J/cm2) was delivered using red light (660±15 nm band pass filter) at irradiance of 100 mW/cm$^2$ as measured with a power meter (model DMM 199 with 201 standard head; Coherent, Santa Clara, Calif.). The fluorescence was measured after each dose of light was delivered. The presence of KI did not produce any difference in SOSG activation (FIG. 4A) while a quenching phenomenon for HPF was observed (FIG. 4B). The reduction in probe activation observed in our system could possibly be explained by the recently reported KI-related effect of decrease of in vitro generation of ROS produced by polymorphonuclear leucocytes (PMN) (see Miyachi, Y. and Y. Nivea, Br J Dermatol, 1982. 107(2): p. 209-14.)

Iodine Generation.

Figure 5:
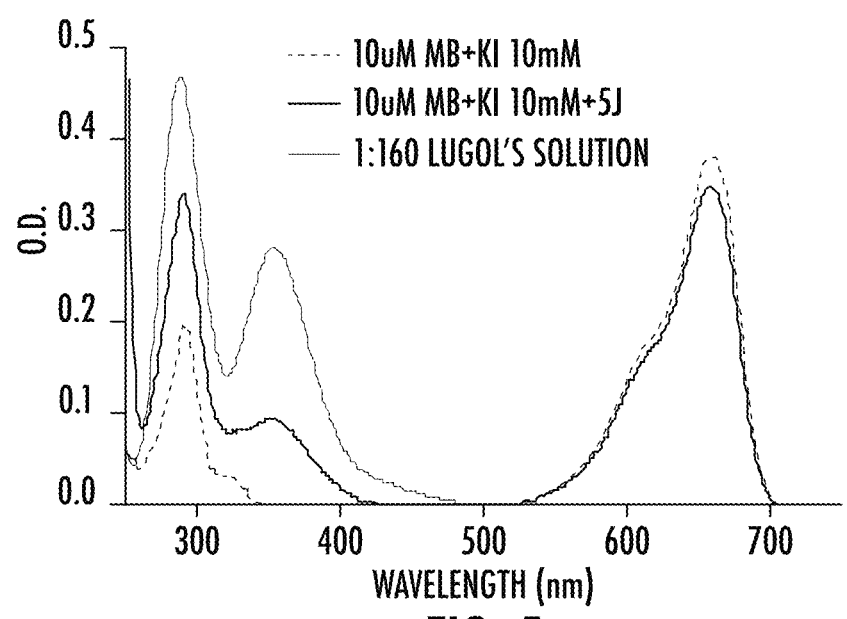
FIG. 5 presents the results of iodine generation experiments.

To verify whether the generation $I_2$ could be responsible for killing the bacteria, the spectra of MB and MB+KI solutions were established before and after shining the light. UV-Vis spectral analysis was carried out using a spectroradiometer (SPR-01; Luzchem Research, Inc., Ottawa, ON, Canada) and showed a peak emission at 365±5 nm. The solutions of MB (10 uM) with and without addition of 10 mM of KI were irradiated with 7 J/cm$^2$ of red light, and afterwards 10$^8$ CFU bacterial cells were added to the light-treated solutions in the range of time 0-30 min. CFU were measured as described above. The generation of iodine species was evaluated by measuring the spectral peak at 348 nm. Our positive control was reference 1:160 Lugol's solutions in PBS combined with MB. As shown in FIG. 5, the production of iodine species was observed when light was delivered at 5 J/cm$^2$, and no iodine-representing peak was observed in the spectra before irradiation of the chemical with light.

Potentiating Effect on Bacterial Killing Produced by Addition of Salt of Alkaline Metal to Fenton Reagent or to $H_2Q_2$ and HPR.

Figure 6A:
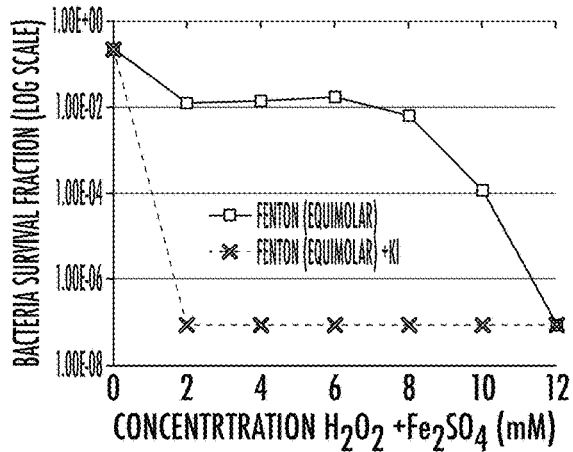
FIGS. 6A, 6B, 6C, 6D are plots illustrating the antimicrobial activity of Fenton reagent (ratio of FeSO4/H2O2 was 1:1) and of a combination (Fenton reagent plus KI) against *S. aureus* (FIGS. 6A, 6C) and against *E. coli*.
Figure 6B:
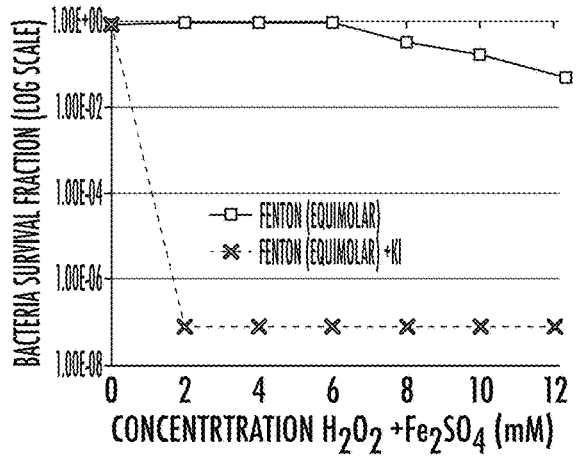
Figure 6C:
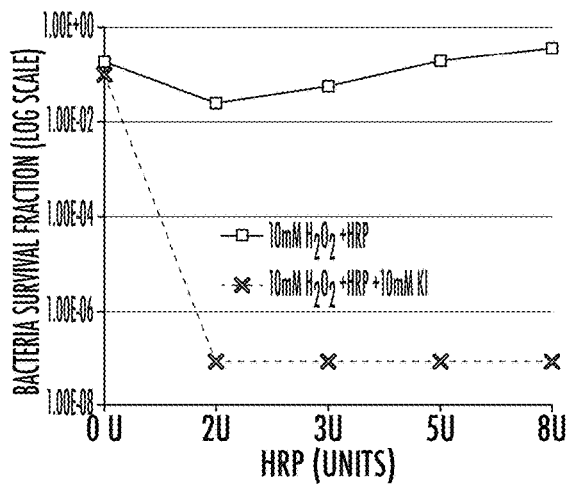
Figure 6D:
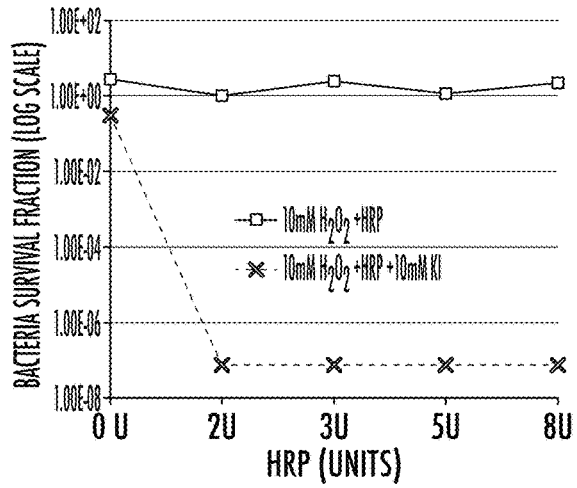

The plots in FIGS. 6A, 6B, 6C, 6D show the antimicrobial activity of Fenton reagent (ratio of FeSO4/H2O2 was 1:1) and of a combination (Fenton reagent plus KI) against *S. aureus* (FIGS. 6A, 6C) and *E. coli*. (FIGS. 6B, 6D). During the preparation to the measurement, suspensions of bacteria ($10^8$ CFU/ml) were incubated at room temperature with various concentrations of Fenton reagent (equal concentrations of $H_2O_2$ and $FeSO_4$) or with 10 mM $H_2O_2$+HRP (0-8 U) with and without addition of 10 mM KI. In both experiments bacterial cells were incubated with reagents diluted in pH 7.4 PBS for 1 hour. At the end of the incubation time 100 µl aliquots were placed in 96 wells from each tube and serially diluted on agar plates to determine CFU.

When Fenton reagent was combined with 10 mM KI, a dramatic potentiation (up to 6 logs) of the antimicrobial effect of the Fenton reaction as observed, similar to prior reports in related art. This could imply HO˙ reacted with KI produces iodide radicals from HO˙, which potentiated bacterial killing in cell suspension. The same dramatic potentiation in bacterial killing (about 6 logs) when we added KI to the reaction $H_2O_2$+horseradish peroxidase (HRP), also substantiating results of similar experiments in related art. The mechanism of action was proposed to be oxidation of iodide anion to iodine radicals by the enzyme-hydrogen peroxide transition state [24] (as originally worked out by Chance in 1943 [25]). (Kohler, H. and H. Jenzer, Free Radic Biol Med, 1989. 6(3): p. 323-39; as originally worked out by Chance B., Adv Enzymol Relat Areas Mol Biol, 1999. 73: p. 3-23).

Relevance of Long-Lived Reactive Iodine Species ($I_2$ or HOI) to Bacterial Killing.

To verify if long-lived species such as molecular iodine ($I_2$) or hypoiodous acid (HOI) could be responsible for increased bacterial killing we added bacteria after completion of light delivery.

Figure 7B:
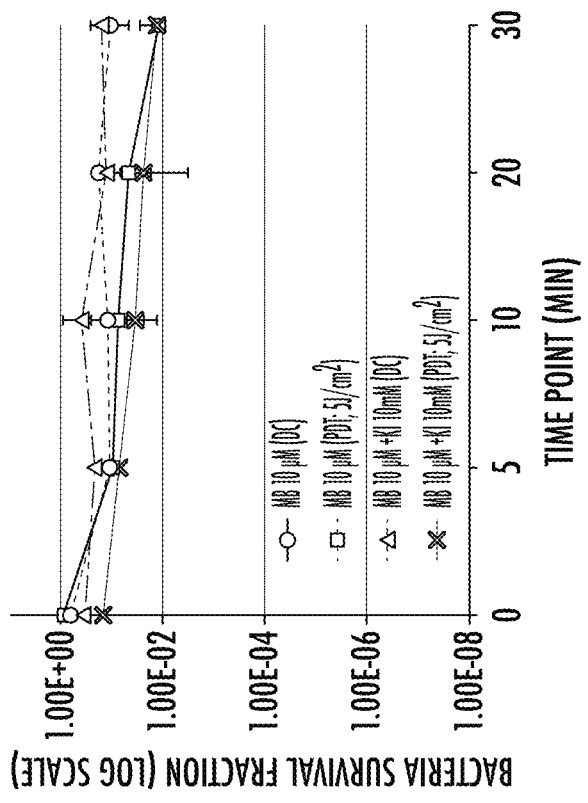
FIGS. 7A, 7B illustrate influence of long-lived reactive iodine species ($I_2$ or HOI) on inactivation of bacteria.
Figure 7A:
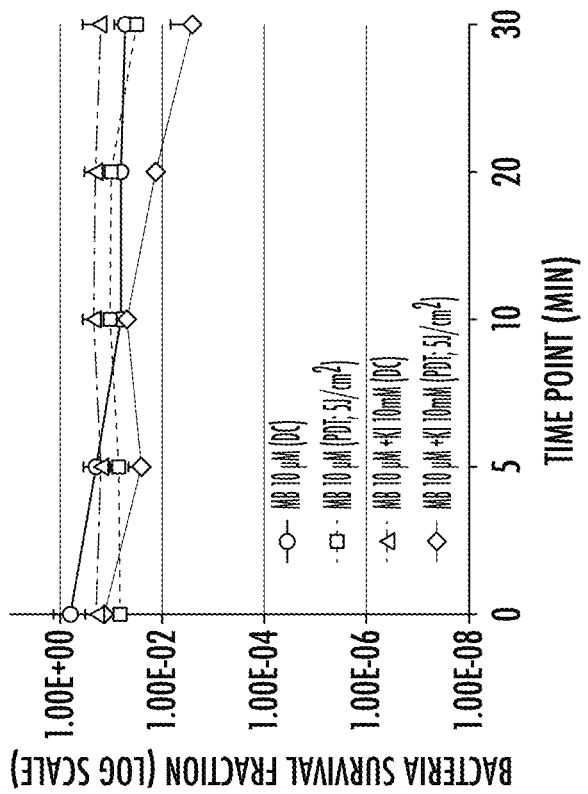

We irradiated with 5 J/cm$^2$ the solutions containing MB or MB+KI to generate the iodine species observed in the spectra described above. Since $I_2$ is a stable molecule, and even HOI is reasonably stable with a measurable half-life, by incubating the cells in a solution that could contain photochemically produced bactericidal concentrations of $I_2$ or HOI, we expected to observe bacterial killing. We added bacterial cells and we evaluated the survival fraction of bacteria in an incubation time range between 5 and 30 minutes. As shown in the plots of FIGS. 7A, 7B we did not observe any bacterial killing in both strains. This demonstrated that even if in our system generated $I_2$ and HOI, there was no evidence that the concentration produced could be responsible for bacterial killing observed in PDI in presence of KI. No killing was observed in dark control.

Example 2: Formation of MCPPS from Fullerene and Salt of Alkaline Metal

In this example, the employ of an MCPPS formed by addition of iodide anion to fullerene material (specifically, a C60 fullerene bisadducts), otherwise singly mediating antimicrobial photodynamic treatment, clearly demonstrated increase of efficacy of the photodynamic treatment as compared with the that utilizing only the fullerene. Studies with members of three different classes of pathogen were carried out to demonstrate the broad-spectrum nature of the approach.

Fullerenes (C60, C70, C84) are a class of closed cage carbon molecules with a large number of conjugated double bonds that efficiently absorb light in the UV and visible spectral regions. The excited singlet state undergoes efficient intersystem crossing giving these molecules a high triplet quantum yield. Pristine fullerenes are highly hydrophobic and insoluble in aqueous media making them largely unsuitable for biological applications. However the fullerene carbon cage can be derivatized by attachment of organic ligands containing suitable functional groups to provide water solubility and to enable the fullerenes to recognize and bind to biological targets such as bacterial cells. One of the most suitable functional groups for both these purposes is the quaternary ammonium group that provides constitutive cationic charges.

The use of fullerenes as single-component PS to mediate a PDI-type treatment may be one of the most promising biomedical applications of nanotechnology. Although their absorption spectrum is mainly in the shorter wavelength regions of the electromagnetic spectrum, which may considered a disadvantage, they have several other properties that make them advantageous. Fullerene molecules have high photostability that makes them resistant to photobleaching that can be the limiting factor in the case of more usual PS derived from tetrapyrrole or phenothiazinium structures. They are particularly effective at mediating Type 1 photochemical mechanisms as opposed to the Type 2 generation of singlet oxygen that dominates other PS.

Irradiation Setup.

UVA light (360+/−20 nm, American Ultraviolet Co, Lebanon, Ind.) was delivered to a spot with diameter 15 cm at an irradiance of 20 mW/cm$^2$. The irradiance was measured using a model IL-1700 research radiometer/photometer (International Light, Inc., Newburyport, Mass.) using a wavelength range of 250-400 nm. White light source at 400-700 nm (Lumacare, Newport Beach, Calif.) was used to deliver light over a spot diameter 3-cm at an irradiance of 100 mW/cm$^2$ as measured with a power meter (model DMM 199 with 201 standard head; Coherent, Santa Clara, Calif.)

Bacterial Strain and Culture Conditions.

Here, the used *A. baumannii* strain had previously been engineered to be bioluminescent using the lux ABCDE plasmid (Dai T. et al., Antimicrob Agents Chemother 2009; 53(9):3929-3934). The used methicillin-resistant *S. aureus* (MRSA) strain was USA300 LAC (Los Angeles County clone), a CA-MRSA strain. The USA300 LAC was chromosomally transduced with the transposon for the bacterial luciferase gene operon lux ABCDE (pAUL-ATn4001 lux-ABCDE Km(r); Caliper Life Sciences, Hopkinton, Mass.) to give USA300 LAC::lux), allowing a real time monitoring of the extent of bacterial infection in living. Both bacterial species were routinely grown in brain heart infusion (BHT) medium supplemented with 50 µg/mL kanamycin in an orbital incubatorovernight. The overnight suspension was centrifuged, washed with phosphate buffered saline (PBS), and re-suspended in fresh BHI medium to a cell density of 10(8) cells/mL (measured by optical density) for experimental use. The bioluminescent *C. albicans* strain used was CEC 749 as described in Enjalbert B. et al. Infect Immun 2009; 77(11):4847-4858. The luciferase reporter was constructed by fusing a synthetic, codon-optimized version of the Gaussiaprinceps luciferase gene to *C. albicans* PGA59, which encodes a glycosylphosphatidylinositol-linked cell wall protein. Luciferase expressed from this PGA59-gLUC fusion was localized at the *C. albicans* cell surface allowing the detection of luciferase in intact cells after the addition of the luciferase substrate, coelenterazine. *C. albicans* was routinely grown at 30° C. on yeast peptone dextrose (YPD) agar and sub-cultured in YPD medium to an optical density of 0.65 at 570 nm, which corresponds to $10^7$ colony forming units (CFU)/mL. This suspension was then centrifuged, washed with phosphate-buffered saline (PBS), and re-suspended in PBS at the same cell density for experimental use.

Iodide-Driven Potentiation of PDI Mediated with Fullerenes.

Three mL of *A. baumannii* or MRSA suspension both at ≈10(8) CFU/mL, or 3 mL of *C. albicans* at ≈10(7) CFU/mL in PBSz were incubated with LC16 at a concentration of 20 uM for 20 minutes. After the incubation time was complete 30 uL of 1M solution of potassium iodide (or PBS as a control) was added to bring the final KI concentration to 10 mM and the suspensions were immediately transferred were into a 35-mm petri dish at room temperature (21° C.). The suspensions were irradiated with the white light Lumacare probe at an irradiance of 100 mW/cm$^2$ or with the UVA lamp at an irradiance of 20 mW/cm$^2$ with the lid of the petri dish removed. During light irradiation, the suspension was gently stirred by a mini-magnetic bar (Fisher Scientific Co., Norcross, Ga.) at 20 rpm. Aliquots of 30 µL of the suspension were withdrawn at 0, 5, 10, 15 and 20 mM, respectively, when 0, 30, 60, 90 and 120 J/cm$^2$ white light or at 0, 4, 8, 12 and 16 min, when 0, 5, 10, 15 and 20 J/cm$^2$ UVA light had been delivered. Light controls received light+KI but no LC15. CFU were then determined by serial dilution on BHI agar (YPD agar for *Candida*) plates by the method of Jett B. D. et al. (Biotechniques 1997; 23(4):648-650). Colonies were allowed to grow for 18-24 h at 37° C. for bacteria and at 30° C. for *Candida*. The in vitro experiments were performed in triplicate.

Figure 8A:
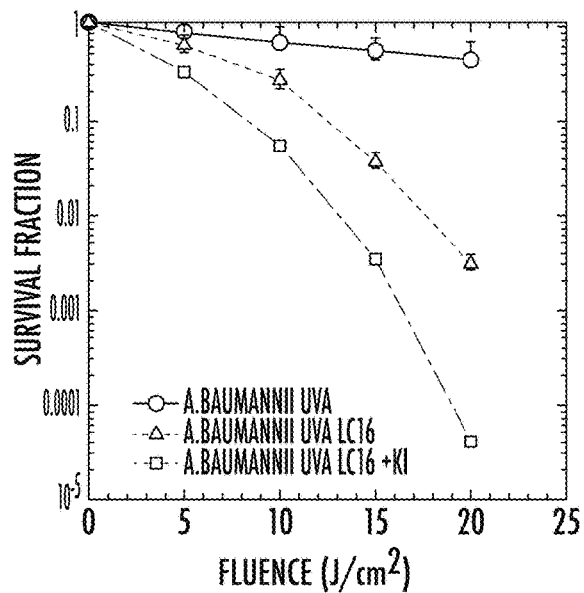
FIGS. 8A, 8B are plots illustrating bacteria inactivation with the use of MCPPS formed by the addition of a salt of alkaline metal to the fullerene (used as a single-component PS) in in vitro antibacterial PDI in *A. baumannii*.
Figure 8B:
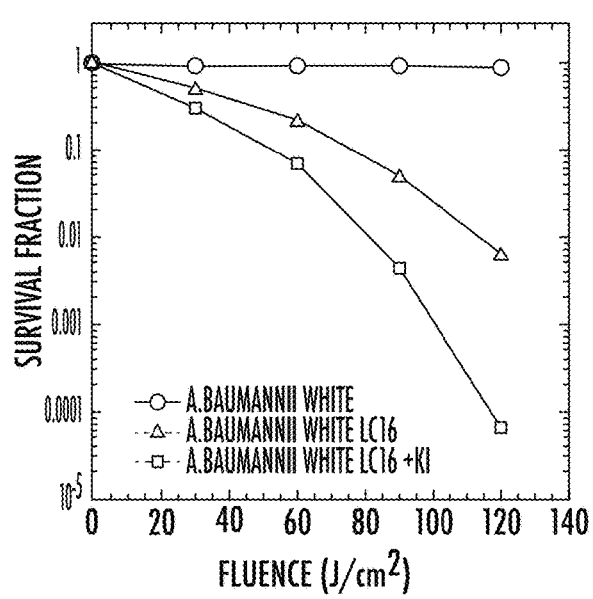

Initially, the use of an MCPPS containing fullerenes and KI for in vitro antibacterial PDI in *A. baumannii* was considered. The curves representing the results are shown for LC16 and LC16 combined with KI, in FIGS. 8(A,B). The fullerenes were excited with white light and with UVA light as there was some evidence that the photochemical mechanism that followed upon fullerene illumination depended on the excitation wavelength. We delivered increasing fluences of light after incubating the bacteria with a constant concentration of 20 µM fullerene with or without the addition of 10 mM KI. The ratio of fluences of UVA or white light employed was roughly in line with the relative absorption coefficients in the spectrum of LC16. This meant that we delivered up to 20 J/cm$^2$ of UVA light, and up to 120 J/cm2 of white light, or six-fold more. Although it is not possible to precisely measure the number of photons absorbed from each light source because of the wide band-widths employed, it is estimated that a 6-fold difference in fluence has occurred. When LC16 was excited by UVA light (FIG. 8A), 1.5 logs of *A. baumanii* at 15 J/cm$^2$ and 2.5 logs at 20 J/cm$^2$ were deactivated. UVA light alone (no fullerene) deactivated less than 1 log even at 20 J/cm2. When 10 mM KI was added to the incubation mixture to form the MCPPS, the bacterial killing was significantly potentiated (up to 2.5 logs at 15 J/cm$^2$, p<0.001, and 4.5 logs at 20 J/cm$^2$, p<0.001). The data with white light excitation are shown in FIG. 2B. There was no significant bacterial killing with white light atones as expected. LC16 at 20 uM excited with white light killed 1.5 logs at 90 J/cm$^2$ and 1.5 logs at 120 J/cm$^2$. The addition of 10 mM KI significantly potentiated the killing with 2.5 logs at 90 J/cm$^2$ (p<0.001) and 4 logs at 120 J/cm$^2$ (p<0.001). The degree of potentiation by KI appeared to be very similar regardless of whether UVA light or white light was used to excite LC16.

Figure 9A:
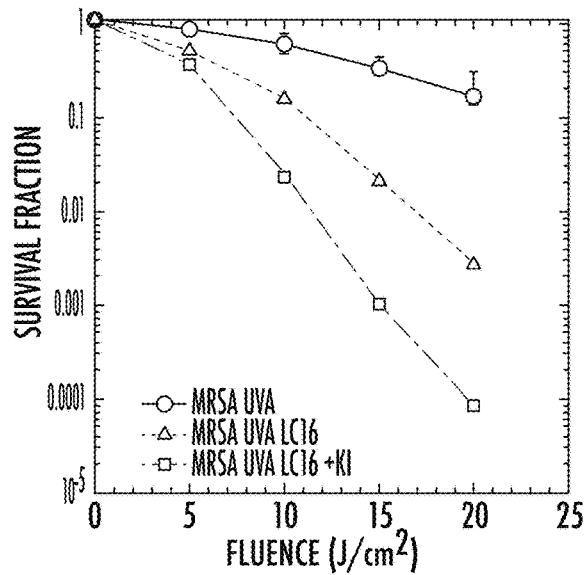
FIGS. 9A, 9B illustrate iodide potentiation of the PDI process in the case of Gram-positive species MRSA.
Figure 9B:
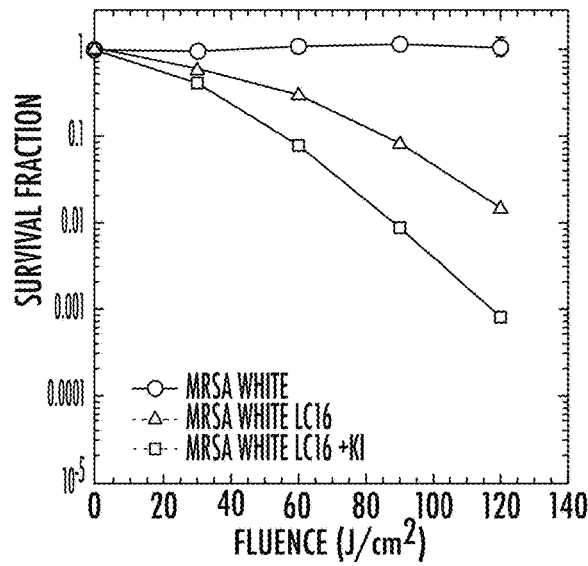

The positive effects of iodide potentiation in the case of Gram-negative *A. baumannii*, prompted the testing of the Gram-positive species MRSA. The data are shown in FIGS. 9A, 9B. With UVA there was more than 1 log of potentiation with KI (from 1.8 to 3 logs of killing after 15 J/cm$^2$; from 2.7 logs to 4.1 logs after 20 J/cm$^2$). With white light excitation there was again about 1 log of potentiation with KI at 90 and 120 J/cm$^2$. These increases were all highly significant (p<0.001).

Figure 10A:
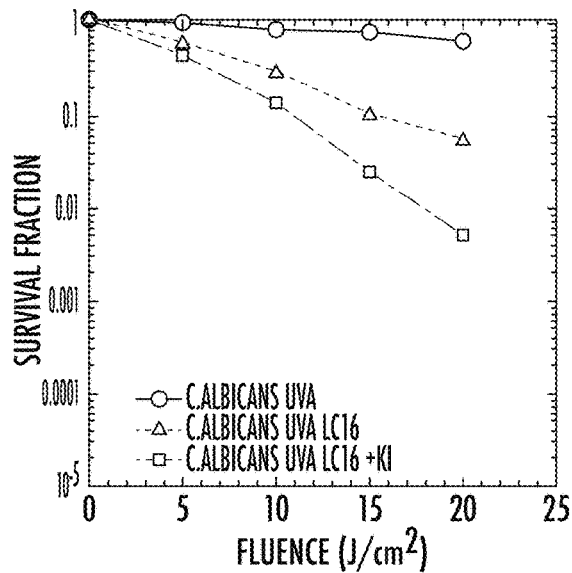
FIGS. 10A, 10B are plots confirming broad-spectrum nature of the enhancement of PDI-process potency due to the use of the MCPPS formed by the combination of the fullerenes and a salt of alkaline metal.
Figure 10B:
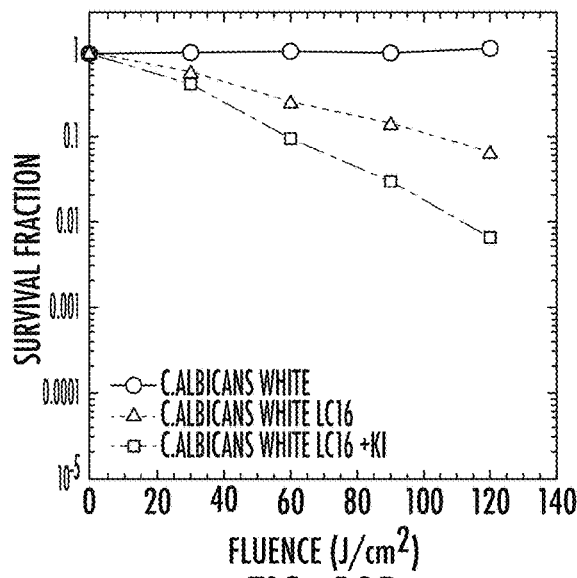

Finally to confirm the broad-spectrum nature of this enhancement of PDI potency due to the use of the MCPPS formed by the combination of the fullerenes and KI, the fungal yeast *C. albicans* was tested. Although the overall killing of *C. albicans* by fullerene mediated PDI was lower that that found for the bacterial species, we nevertheless were able to demonstrate a significant (p<0.001) potentiation by addition of KI (almost 1 log more killing) with both UVA light (FIG. 10A) and with white light (FIG. 10B).

The above-discussed experiments prove for the first time that the potency of PDI conducted with the use of a multi-component potentiated fullerene material including the combination of a catonic fullerene having an additional tertiary amine chain s with an inert and non-toxic salt is substantially higher than that conducted with the use of only fullerene material. The mechanism of action of the potentiation of fullerene-mediated PDI by addition of iodide anion is incompletely understood. There potentially could be as many as three separate mechanisms operating. These are: (1) Iodide anion could act as an additional source of electrons thus potentiating the Type 1 electron transfer photochemical mechanism of the photoexcited fullerene generating more bactericidal ROS such as hydroxyl radicals; (2) Iodide anion could undergo a one-electron oxidation by the electron transfer to the photoexcited fullerene to form iodide radicals and fullerene radical anions which are expected to be bactericidal; (3) Iodide anion could be oxidized either by Type 1 or by Type 2 photochemical mechanisms to form molecular iodine which is known to be bactericidal. Further studies are actively under way in our laboratory to tease apart the relative contributions of each of these mechanisms to the iodide potentiation of the microbicidal effect.

Notably, the potentiating effect of iodide was observed to about the same extent in the three different classes of microbial cells. The decacationic fullerene was designed to bind and penetrate different classes of microbial cells. It is known that Gram-positive bacteria have permeable cell walls, while fungal cells have a less permeable cell wall structure and Gram-negative bacteria have an impermeable cell wall. However the permeability barrier of Gram-negative bacteria can be overcome by polycationic molecules that disturb the lipopolysaccharide structure by displacing the divalent cations $Ca^{2+}$ and $Mg^{2+}$. The permeability of microbial cells to iodide anion has not been much studied. Although mammalian cells accumulate iodide via the sodium/iodide symporter (highly expressed in the thyroid), only a few rare marine bacterial species have been found to accumulate iodide. At present we believe that the chief site of action of iodide is extracellular, but this remains to be experimentally proved.

One of the chief attractions of an inert salt (such as potassium or sodium iodide, or $KNO_2$, $NaNO_2$, or other salts listed in Table 1) as an adjuvant to potentiate the antimicrobial effect of fullerene-mediated PDI is the lack of toxicity of both the chosen salt and fullerene. (Sherer T. T. et al., J Toxicol Environ Health 1991; 32(1):89-101; Henry T. B. et al. Curr Opin Biotechnol 2011; 22(4):533-537).

Example 3: Potentiation of Antimicrobial Effects of Titanium Dioxide Photocathalysis with Intert Salt of Alkaline Metal Ultraviolet A excitation of titanium dioxide nanoparticles (a wide-band gap semiconductor) in a process called photocatalysis, produces reactive oxygen species that can destroy many classes of microorganisms. As disclosed below, it was demonstrated for the first time that the addition of the non-toxic inorganic salt (such as, in one example, potassium iodide) to $TiO_2$ (referred to as titania) excited by UVA, potentiates antimicrobial photocatalysis in that it potentiates the killing of Gram-positive, Gram-negative bacteria and fungi by up to 6 logs.

The extent of microbial killing depended on the concentration of TiO2, the delivered fluence of UVA light, and critically on the concentration of added KI. Under the conditions we employed that microbial killing obtained by using TiO2 and UVA light alone was minimal, less than 1 log even with 5 mM TiO2 and 20 J/cm2 of UVA. However when iodide was added at 10 mM there was 5 logs of killing with *E. coli*, and with 100 mM iodide there was eradication (>6 logs killing) with only 5 J/cm2.

Chemicals and Materials.

All chemicals were used as received without any further purification. TiO2 P25 anatase, potassium iodide (KI), Lugol's solution, and all other reagents were purchased from Sigma-Aldrich (St. Louis, Mo.) unless otherwise indicated. Brain-heart infusion (BHI) and yeast peptone dextrose (YPD), Singlet oxygen green sensor (SOSG) for singlet oxygen detection and hydroxyphenyl fluorescein (HPF) for hydroxyl radical were purchased for were purchased from Fisher Scientific. 0.5% starch solution was purchased from Ricca chemical company (Arlington, Tex.). TiO2 stock solution was prepared in distilled H2O (dH2O) and stored at 4° C. in the dark for no more than 24 h prior to use. KI solution was prepared in dH2O as required immediately before experiments. All the PCD experiments were carried out using 24-well plate under magnetic stirring except ROS probe experiments.

Microbial Strains and Culture Conditions.

The following microbial strains were used in the experiment: methicillin-resistant *Staphylococcus aureus* (MRSA US-300), *Escherichia coli* (*E. coli*) K12, and *Candida albicans* (CEC 749) [PMID 19687206]. Planktonic MRSA, *E. coli* and *C. albicans* were cultured in BHI broth in Erlenmeyer flask overnight in incubator-shaker with speed of 150 rpm. An aliquot of 1 ml from an overnight suspension was refreshed in fresh BHI (MRSA and *E. coli*) for 2 hours at 37° C. or YPD (*C. albicans*) for 4 h at 30° C. to reach mid-log phase. Cell numbers of MRSA and *E. coli* were estimated by measuring the optical density (OD) at 600 nm (OD of 0.6=10^8 cells/ml). Cell number of *C. albicans* was assessed with a hematocytometer. The microbial cells suspension was centrifuged, washed, and resuspended in pH7.4 phosphate buffer (PB) to arrest microbial growth and used (10^8 CFU) for the in vitro experiments.

UVA Light Source.

UVA light was delivered using a 360 nm Light-emitting diode (LED) light source (Larson Electronics LLC, Kemp, Tex.). Emission spectrum measurement of this lamp by a spectroradiometer (SPR-01; Luzchem Research Inc. Ottawa, ON, Canada) showed a peak emission at 360±5 nm. By manipulating the distance between the UVA LED and the target to be irradiated, the irradiance was. The irradiance was 16 $mW/cm^2$, measured using a model IL-1700 research radiometer/photometer (International Light Inc., Newburyport, Mass.) over the wavelength range of 250-400 nm.

Potentiation of TiO2 Photocatalytic Disinfection by Addition of Potassium Iodide In Vitro.

Figure 11A:
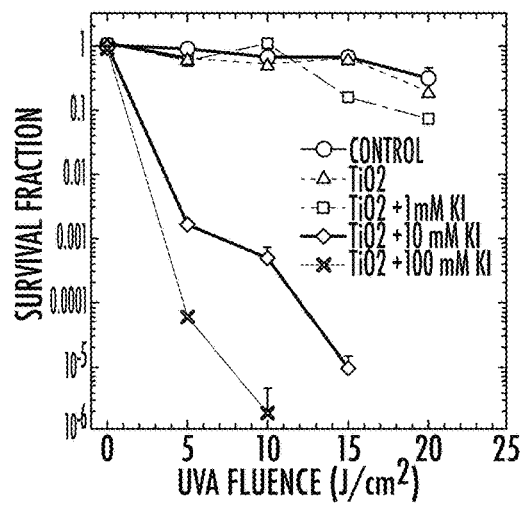
FIGS. 11A, 11B, 11C, 11D, 11E are plots showing the results of potentiation of antimicrobial $TiO_2$ photocatalysis of microbial cells with addition of inert salt of an alkaline metal.
Figure 11B:
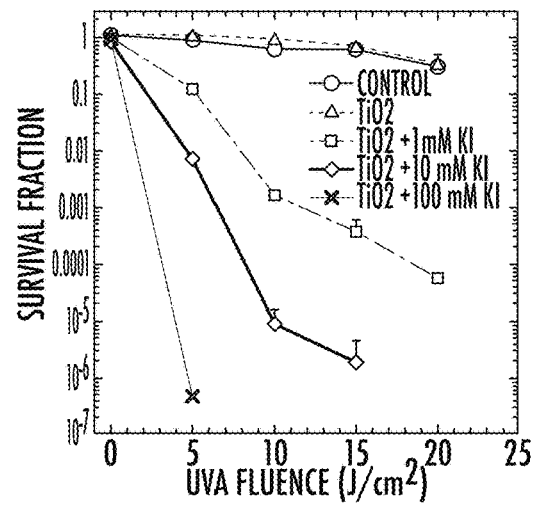
Figure 11C:
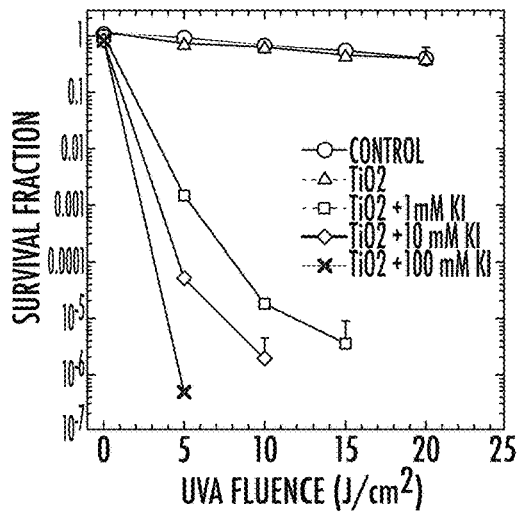
Figure 11D:
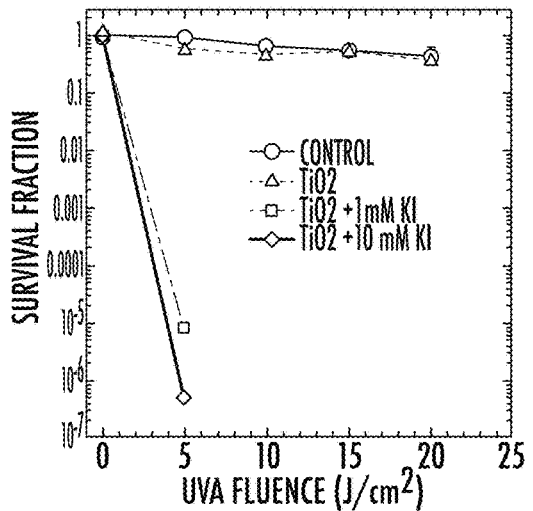
Figure 11E:
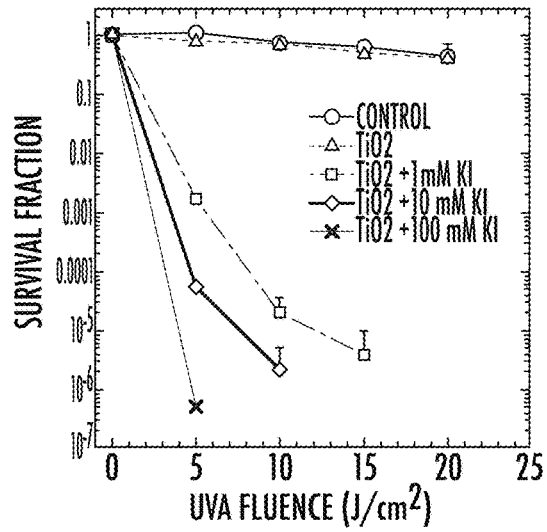

When MRSA cells (10(8) CFU/mL; Gram-positive bacteria, grown overnight at 37° C. (30° C. for *C. albicans*) and bacteria were refreshed for 2-4 hours before being collected through centrifugation and suspended in pH7.4 phosphate-buffer) were mixed with various concentrations of the $TiO_2$ (0 mM, 1 mM, 5 mM) in 24-well plate under magnetic stirring at room temperature, and either left in the dark or irradiated with UVA light at room temperature using a UVA LED to deliver 0-20 $J/cm^2$ light, the viability of cells reached only 1 logs of killing at 20 $J/cm^2$. However, there was a light-dose dependent increase when additional KI (0, 1, 10, or 100 mM) was added to the mixture. The antimicrobial effect was potentiated by 3-5 logs of extra killing (FIG. 11A). When the experiment was repeated with *E. coli* (10(8) CFU/mL; Gram-negative bacteria) there was a light dose-dependent killing, with $TiO_2$ and UVA light alone giving over 6 logs of killing at 20 $J/cm^2$. However when 10 mM KI was added, there was an extra 1-3 logs of bacterial killing on top of that seen with photocatalysis alone (FIG. 11B). When the experiment was repeated with 10(7) CFU/mL of *C. albicans* (fungal yeast) we found similar results. With $TiO_2$ and UVA light alone there was up to 2 logs of killing, but this was increased by 3-5 logs of additional killing by the addition of different concentrations of KI (1-100 mM) to the mixture. Initial conditions of experiments were as follows: FIG. 11A: $TiO_2$ 1 mM on MRSA (10(8) cells/mL); FIG. 11B: $TiO_2$ 5 mM on MRSA (10(8) cells/mL); FIG. 11C: $TiO_2$ 1 mM on *E. coli* (10(8) cells/mL); FIG. 11D: $TiO_2$ 5 mM on *E. coli* (10(8) cells/mL); FIG. 11E: $TiO_2$ 5 mM on *C. albicans* (10(7) cells/mL).

Bacteria Inactivation after Irradiation with Light is Over.

Figure 12:
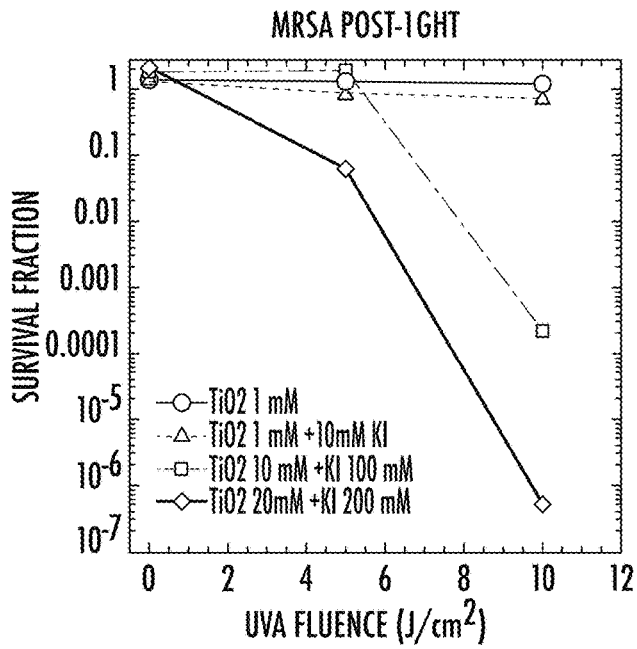
FIG. 12 illustrates deactivation of bacteria added to photoactivated $TiO_2$ after the irradiation was over. $TiO_2$ (1.10, and 20 mM) was stirred with KI (0, 100 or 200 mM) under UVA light (10 J/cm$^2$) on MRSA (A) cells (10(8) cells/mL) were then added at 5 minutes after the end of the illumination and incubated for 1 hour. Values are means of 3 repetitions and bars are SD.

To investigate how much of the synergistic killing was due to production of a relatively long-lived stable antimicrobial species, the microbial cells were at different times after completion of light delivery. FIG. 12 shows that when MRSA cells were added 5 minutes after the light-treatment to a suspension of TiO2 that had been treated with 10 $J/cm^2$ of UVA light in the presence of 10 and 100 mM iodide there was about 3 and 6 logs of killing, but no killing at all without iodide and with low concentration (10 mM) of iodide. When the bacteria were added to the irradiated suspension 30 min after the end of the illumination period there was the same degree of killing, the killing effect could last for more than 48 hours (data nor shown).

ROS Fluorescence Probes.

In order to gain some information on whether a specific reactive oxygen species produced by the illuminated $TiO_2$ was responsible for oxidizing the iodide, we used two fluorescence probes for ROS that we had previously used in photodynamic therapy studies discussed above to determine whether their activation would be quenched by addition of iodide. ROS probe experiments were performed in 96-well clear-bottom-black plates without magnetic stirring. A final concentration of 5 μM SOSG or HPF was added to 1 mM $TiO_2$ suspension with or without the addition of 100 mM KI in 100 μl PB per well. Probe was illuminated with UVA light ($TiO_2$ (0, 0.1 or 1 mM) was illuminated with UVA light (0-7.5 J/cm2) in the presence of KI (10 mM). Fluorescence was measured in plate reader after each does of light had been delivered of light. The fluorescence intensity was determined using a fluorescent plate reader (SpectraMax M5 plate reader; Molecular Devices, Sunnyvale, Calif.) set at ex/em=504/525 nm for SOSG and ex/em=490/525 nm for HPF, respectively. A range of light doses (0 to 7 J/cm2) was delivered using UVA LED (360±5 nm) at an irradiance of 16 mW/cm$^2$ as measured).

Figure 13A:
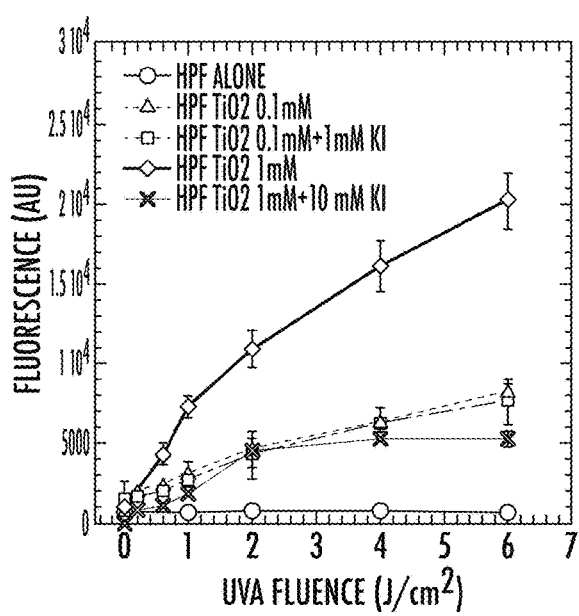
FIGS. 13A, 13B illustrate activation of ROS-specific fluorescence probes by photoactivated $TiO_2$.
Figure 13B:
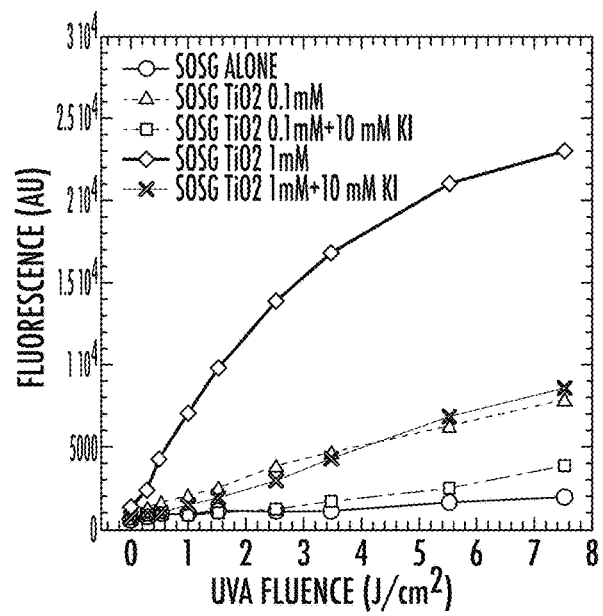

SOSG is relatively specific for singlet oxygen and HPF is relatively specific for detecting hydroxyl radicals. FIG. 13A shows that there was modest but significant quenching of light-activated SOSG fluorescence by addition of 10 mM bromide. FIG. 13B shows that in contrast there was also significant quenching of the photoactivation of the HPF probe.

Iodine Generation.

Figure 14B:
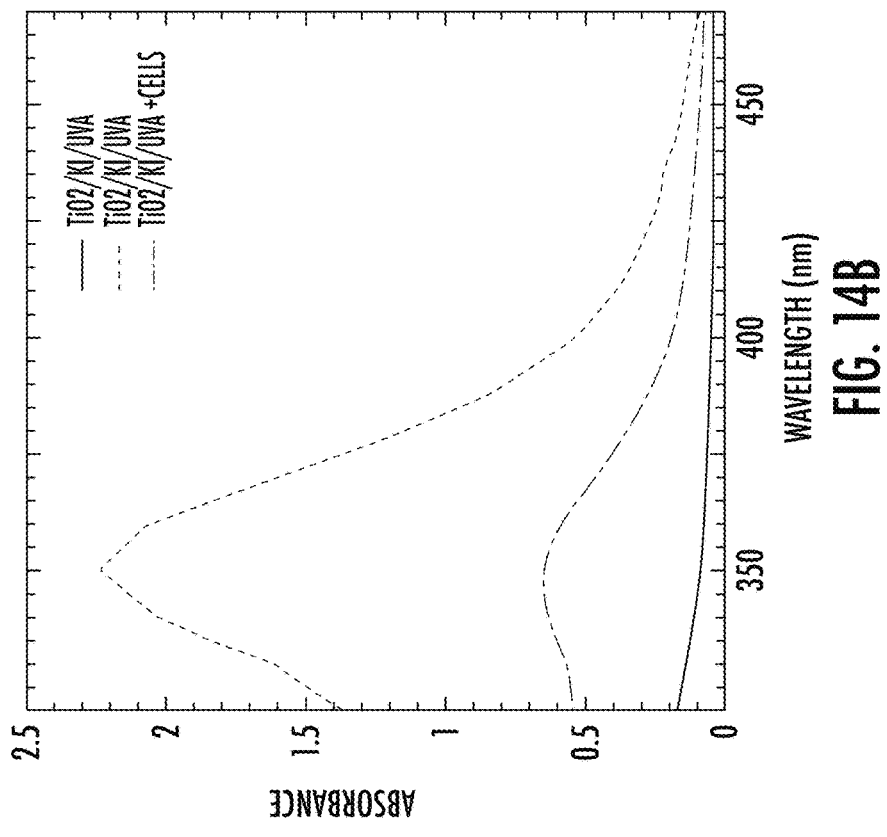
FIGS. 14A, 14B illustrate $I_2$ generation during and post-TiO2 photocatalysis in the presence of KI. Suspension of $TiO_2$ (10 mM) in the presence of KI (100 mM) were stirred with of without bacteria cells (10(8) cells/mL) while being exposed to increasing fluences of UVA light. Supernatant were collected after 5 minutes centrifuge (4000 rpm). Absorbance of $I_2$ was measured using UV-VIS spectrometer.
Figure 14A:
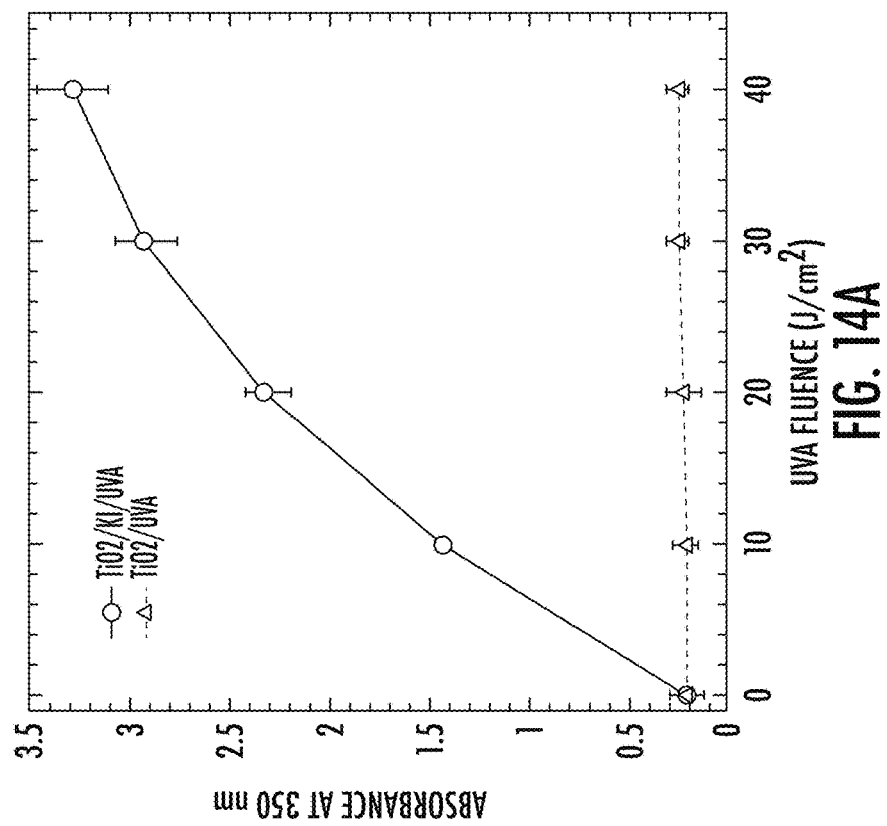

In reference to FIGS. 14A, 14B, I2 generation in a solution containing 1 mM TiO2 and 100 mM KI was detected using UV-visible spectrometer. The spectrum of TiO$_2$/KI suspension was centrifuged at 3500 rpm for 5 mins after shining 0-40 J/cm2 of UVA light. As a reference, spectra were obtained from a 1:200 dilution of Lugol's solution in PB. The UV-Vis absorbance showed a significant increase of I2 at light-dose dependent when shining UVA light 0-40 J/cm$^2$.

It is appreciated that this embodiment of the invention addresses a solution to a long-standing problem of bacterial colonization of medical devices in conjunction with device-surface modification technologies (such as that employing a formation of a thin layer of TiO$_2$ on a surface of a biomedical device to exploit self-disinfecting activity of TiO$_2$). In practice, a surface of a biomedical device such as a dental tool, for example, covered with titania is additionally treated with a salt of alkaline material (or another potentiating component listed in Table 1) prior to triggering the PDI process with irradiating light, to increase a degree of such disinfecting activity by at least one order of magnitude, preferably two orders of magnitude, more preferably three orders of magnitude, even more preferably four orders of magnitude and to reduce the survival fraction of bacteria on such surface by a corresponding factor.

Example 4: Potentiation of Light-Activated PDI Process with Sequential Treatment of Bacteria with Components of MCPPS A colony of UTI89-lux (a persistent uropathogenic *Escherichia coli* (UPEC) isolate from humans) was inoculated in a 50 ml culture in erlenmyer flask and grow in 37° C. incubator-shaker for 16 hours to stationary phase. Cultures were diluted 1:100 in the M63 media and pipetted (100 μl of each) into each well of 12-well plate with a piece of unbreakable plastic membrane (3 cm*3 cm) in the middle of the well vertically. 3 ml M63 media were added to each well of the 12-well plate for a 37° C. overnight incubation under cover. The plastic membranes were transferred to a new 12-well plate containing fresh M63 media every 24 hours for 5 days. Before the PDI experiments, the plastic membranes growing biofilm were removed and washed with PBS, then vigorously shaken out the liquid over a waste container to remove planktonic cells.

According to the idea of the invention, the biofilm membrane was first incubated in contact with a single-component PS (in this case, a 100 uM Methylene Blue solution in PBS for 30 mins in the dark) and then brought in contact with a potentiating chemical component of one of the MCPPS as discussed above. In this case, specifically, after the incubation the biofilm membrane was washed with PBS twice and inserted in a new 12-well plate with 50 mM or 100 mM KI solution in PBS. 10 J/cm2 660 nm laser light was delivered via a optic fiber directly in the solution with irradiance of 30 mW/cm2 to irradiate the biofilm. After PDI experiments, the bacteria cells on biofilm was transferred to 1 ml PBS by scratching with inoculation loop and pipetted into single cells solution. 100 ul aliquot of the biofilm cells solution was serially diluted 10-fold in PBS to give dilutions of 10-1 to 10-5 times in addition to the original concentration, and 10 μl aliquots of each of the dilutions were dropped on square BHI agar plates. Colonies were counted and colony forming units (CFU) were calculated according to (# of colonies× dilution factor)/volume plated=CFU/ml. Survival fractions were routinely expressed as ratios of CFU of microbial cells treated with light and a salt of alkaline metal (or the salt of alkaline metal in the absence of light) to CFUs of microbes treated with neither. Each experiment was performed at least three times.

Figure 15:
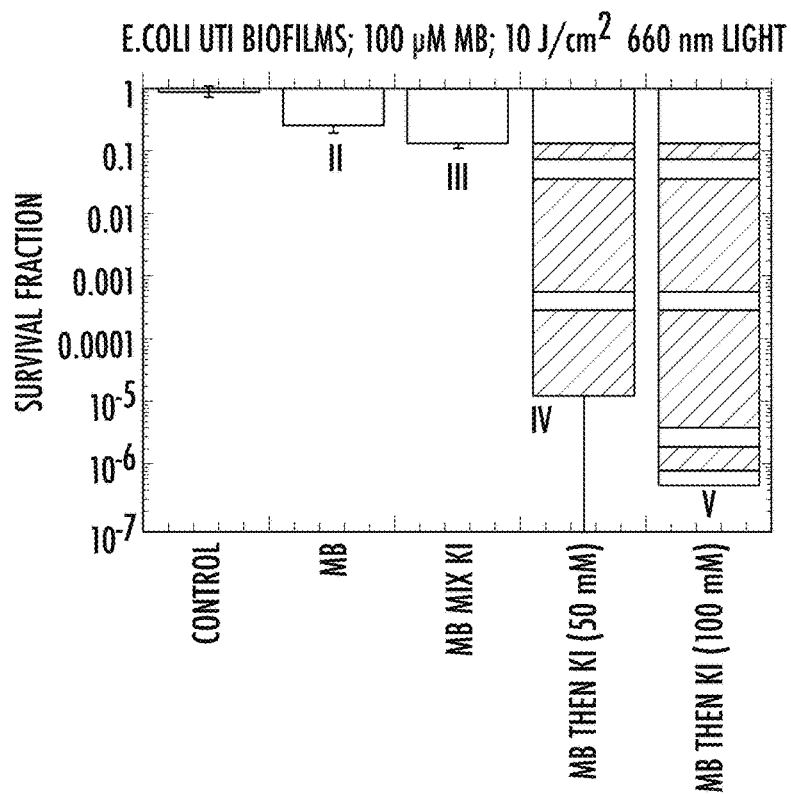
FIG. 15 provides a bar plot illustrating advantages of sequential treatment of bacteria with components of an MCPSS, defined according to the idea of the invention, on increasing the efficiency of the MCPSS-mediated process of PDI.

The results shown as II in FIG. 15 show that the mixture of high concentration of MB and KI killed 2 log of biofilm cells once such mix was applied following the irradiation with light at 660 nm. However, even more potent PDI effect was demonstrated by eradication of biofilm with a two-steps, sequentially performed procedure: incubation of a biofilm with the single-component PA followed by addition of a potentiating chemical composition (such as a salt of alkaline material, for example a 50 mM or 100 mM KI solution, III and IV, respectively) and irradiation with light at a predefined wavelength. Such embodiment of the PDI implemented sequentially according to the idea of the invention reduced the population of the treated bacteria by 4 to 5 or more orders of magnitude as compared to the already improved results (II) achieved due to the potentiation of the MB-mediated PDI with the salt of the alkaline metal. It is appreciated, therefore, that s a result of practical use of one implementation of the method of the invention, when the PDI process is triggered after the target bacteria (which may be located on some surface for example, a surface associated with a catheter, or another medical tool such as scalpel, or a biological tissue, for example skin) has been sequentially pre-treated (soaked or dampened or otherwise brought into contact) with, a) first, only one component of the pre-determined MCPPS, and then h) another, complementary component of the pre-determined MCPPS, the degree of bacterial inactivation is increased at least 100 times (preferably 1,000 times; more preferably 10,000 times; and even more preferably by 5 orders in magnitude) as compared with the case when pre-treatment of such bacteria is effectuated with the whole MCPPS at once (that is, when all chemical compositions comprising the MCPPS are brought into contact with the bacteria at the same time, for example as a mix). Additional Examples of Use of the Method Far Potentiating the It is appreciated that the use of embodiments of PDI-processes (employing complex MCPPS's of the invention to increase potency of the PDI) in combination with various medical/dental tools and specifically-designed photonic systems (such as those, for example, described in WO 2014/004752) is within the scope of the invention.

For example, practical uses of potentiation of photoactivated titania with a salt of alkaline metal can be envisioned to depend on whether the salt is free in solution around the titania; or whether the salt is packaged together with the titania nanoparticles in some sort of hybrid nanostructure. In one form, according to an embodiments of the invention, such hybrid nanostructure (referred to herein as a "nanocell") is similar to a liposome, and includes a vesicle formed from a spherical lipid bilayer, but instead of containing a just an aqueous interior like a regular liposome, the nanocell encapsulates one or more nanoparticles (such as $T_iO_2$ P25) and an aqueous solution of the salt (such as 100 mM KI, for example). Such nanocell would release reactive iodine species after being photoactivated. It another embodiment, a hybrid nanostructure including a $T_iO_2$ nanoparticle coated with an insoluble iodide salt (for instance silver iodide) is created to form a slightly bigger nanoparticle. The applications of this technology include photoactivated antimicrobial surfaces, where the iodide solution is most likely to be used. Here, just before the surface is activated by light, a solution of iodide is sprayed onto the material. When used with implantable medical devices, such as artificial joints or any indwelling device (such as endrotracheal tubes, catheters or access ports, to name just a few), such approach allows for sterilization of the devices without the need to removal from tissue via surgery. While typically the sterilization process is difficult without unacceptable damage to the surrounding tissue, the embodiment of the invention includes a device already pre-coated with $T_iO_2$, while the solution of the identified salt and PDI-process-triggering light are delivered to the surface of the device. In a related embodiment, the same approach is used in dentistry for sterilization of root canals (endodontics) where the combination of $T_iO_2$ and the potentiating salt could be added into the canal and activated with light (via a fiber-optic cable, for example). Nasal decontamination of MRSA is another application where a gel containing both $T_iO_2$ and the potentiating salt is rubbed inside the nose followed by tight activation. In cases where hybrid nanostructures are used, these can be made to be injectable. For instance the $T_iO_2$/salt nanocells could be injected into tumors, into sites with localized infections (abscesses), or into tissue that is required to be destroyed. Light could be delivered via a fiber optic to activate the system.

Figure 16:
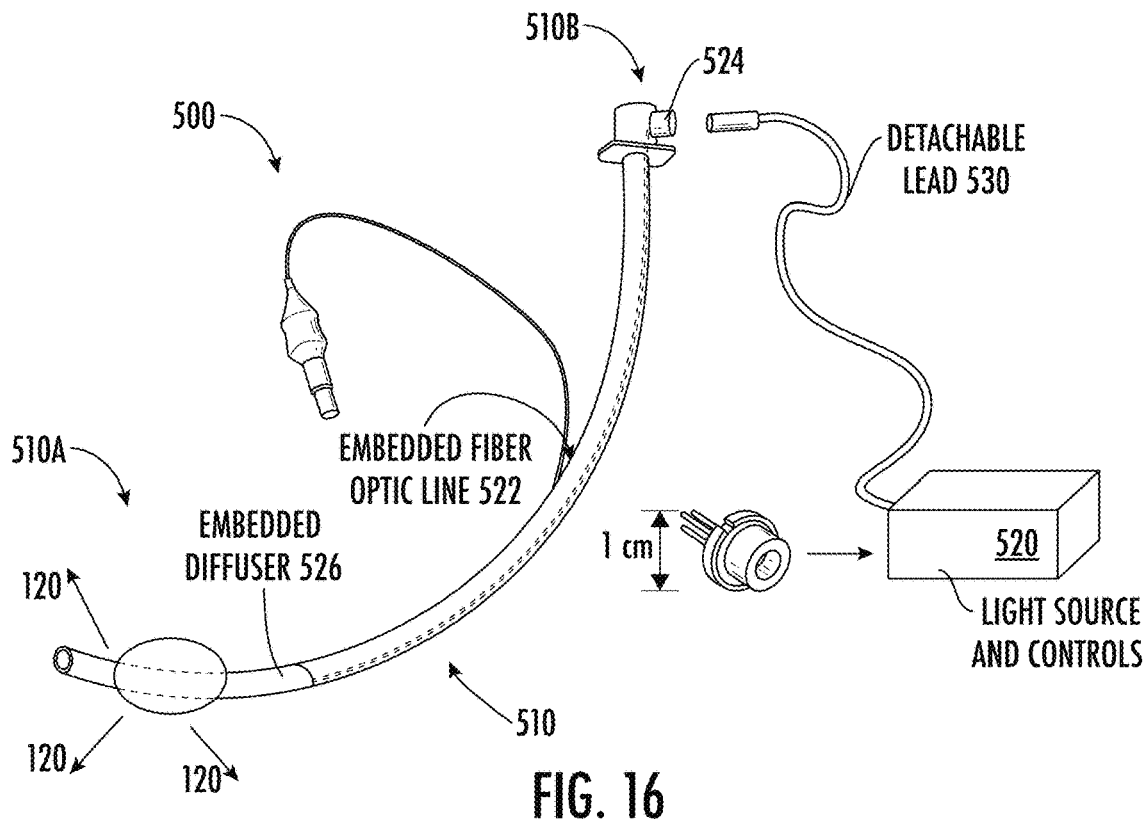
FIG. 16 is a schematic diagram of a device for use with a method of the invention.

In a related embodiment, the method of the invention is practiced with a photonic system such as a catheter specifically-structured to contain in its body a passage, through which the multi-component photosensitizer material is delivered to the targeted area (in a form of a solution, for example) and a fiber-optic (FO) cable or waveguide, through which the triggering light is guided to the region of interest (ROI) where the delivered material is located. One example 500 of such catheter is shown in FIG. 16 and described in detail in WO2014/004752, the entire disclosure of which is incorporated herein by reference. Here, the device of the invention has a tubular wall and includes a catheter or tube or stent or shunt 510 having distal and proximal ends 510A, 510B and a source of excitation power 520 that is external to and, optionally, removably connectable to the proximal end 510b of the tube 510 via a detachable lead 530. The catheter or tube 510 contains an optical fiber line (or, alternatively, a channel waveguide line) 522 embedded in the tube 510, a port 524 of which is adjacent to and/or cooperated with the proximal end 510b. The catheter or tube 510 also contains an optically-diffusing element 526 implanted or embedded in or at the distal end 510A. In one embodiment, the light-diffuser 526 and/or the tube 510 is adapted to form a substantially spatially-uniform distribution of light output. The source 520 (such as, for example, a light source and electronic circuitry adapted to effectuate the operation of the light source) transmits the excitation power (in one embodiment—the electro-magnetic radiation and, in particular, light), through the lead 530 towards the port 524, when connected, and further down the fiberoptic line 522 towards the diffuser 526. The diffuser 526 out-couples light 120 towards the surrounding medium in which the distal end 510a is inserted or implanted. While the optical fiber line 522 is generally passing through and along the wall of the tuber 510, in a specific embodiment shown in FIG. 6 such line 522A is structured as a three-dimensional spiral extending, in the wall of the tube 510, between the proximal and distal ends 510A, 510B and establishing optical communication between the port 524 and the diffuser 526. The spiral-shaped fiber optic line 522 is, optionally, built in the wall of the tube 510 during the process of tube manufacturing. Alternatively, the fiber optic line 522 is wound or coiled around an existing tube and overcoated (to laminate the line 522) with a plastic overlayer the properties of which (including mechanical properties and biocompatibility) are similar to those of the material of the tube 510. In a related embodiment (not shown), no separate FO-cable may be required, and the walls of the catheter itself (its sheath, for example) are configured to guide light towards a region of interest (ROI) where the target bacteria are located.

In another related embodiment, the implementation of invention as discussed in Example 1 was extend to in vivo studies in a murine infection model of burn and carried out with the use of bioluminescent MRSA and in vivo imaging. The goal here was to verify the increase of the efficacy of PDT-process of bacterial killing by adding KI to MB in an in vivo infection model.

Figure 17A:
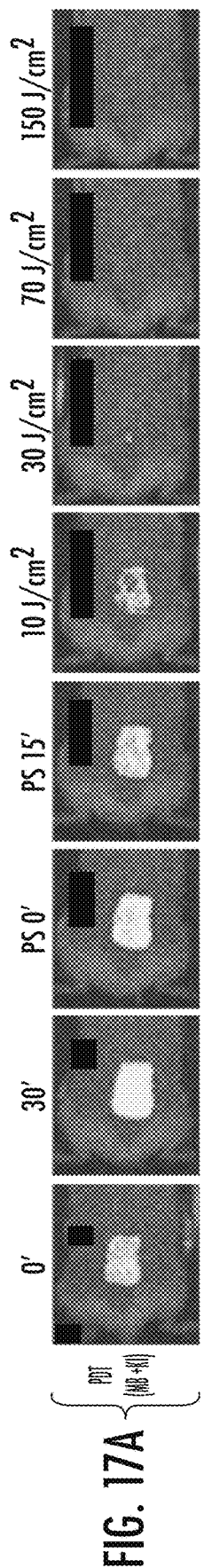
FIGS. 17A, 17B, 17C, 17D, 17E represent a set of bioluminescence images, each taken over time, of a burn infected with MRSA and treated according to an embodiment of the invention.
Figure 17B:
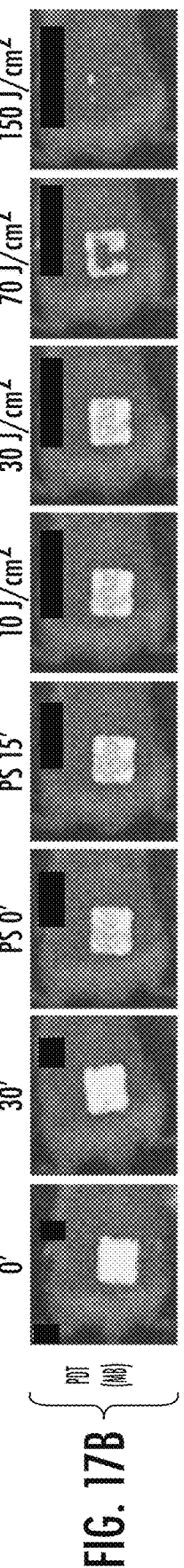
Figure 17C:
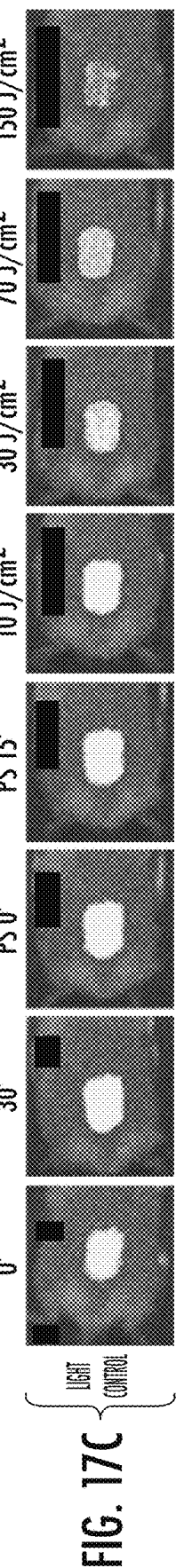
Figure 17D:
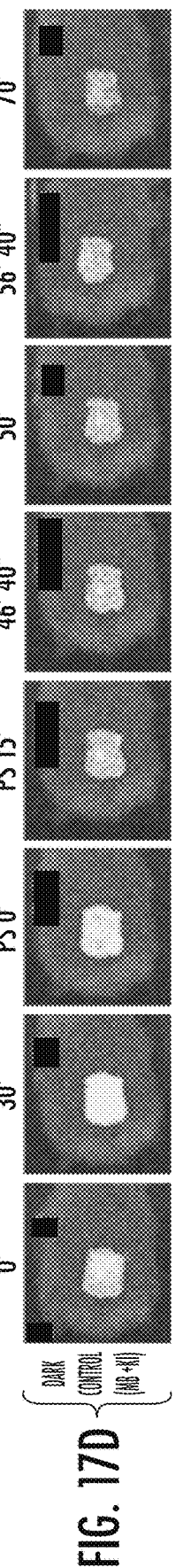
Figure 17E:
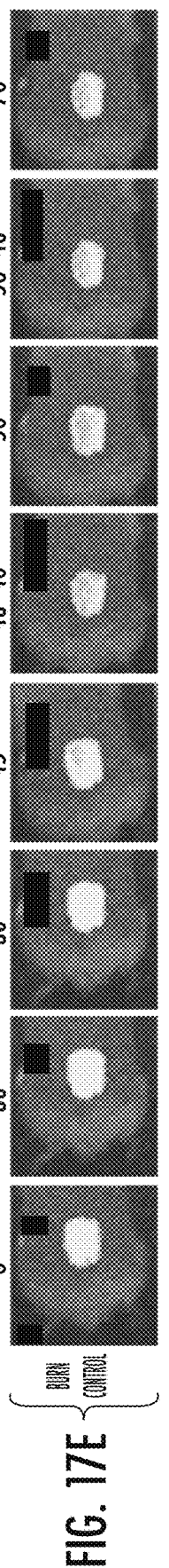

In reference to FIGS. 17A, 17B, 17C, 17D, 17E the infected burn was treated with 50 uM of MB, with and without the addition of 10 mM of KI and excited with 660 nm light; up to 150 J/cm² while the control groups were dark controls with the same amount of MB+KI and light alone control received 660 nm light to 150 J/cm². Aggregately, FIGS. 17A through 17E represent a set of 5 representative bioluminescence image time courses from the burn (each time course from a single mouse in each of the 5 groups) infected with MRSA. The bacterial bioluminescence was largely preserved in the infected burn control (FIG. 17E) during the treatment with light alone (FIG. 17C) and in dark controls of MB+KI (FIG. 17D). In contrast, PDT gave a light dose-dependent reduction of bacterial bioluminescence from mice wounds treated with MB (FIG. 17B) or MB+KI (FIG. 17A) during the PDI treatment. The amount of light required to eradicate bacteria from the wound was much less when the bacteria treated with the (MB+KI) solution was irradiated than when MB alone was used to pre-treat bacteria prior to irradiation.

FIG. 18 provides the light-dose-response curves of all groups. Each curve represents the average±SEM of bacterial bioluminescence in each group (n=6). PDT using MB induced a decrease of around 2 log unit in bacterial bioluminescence while the MK+KI induced up to 3.5 log unit reductions during the same time.

Figure 19G:
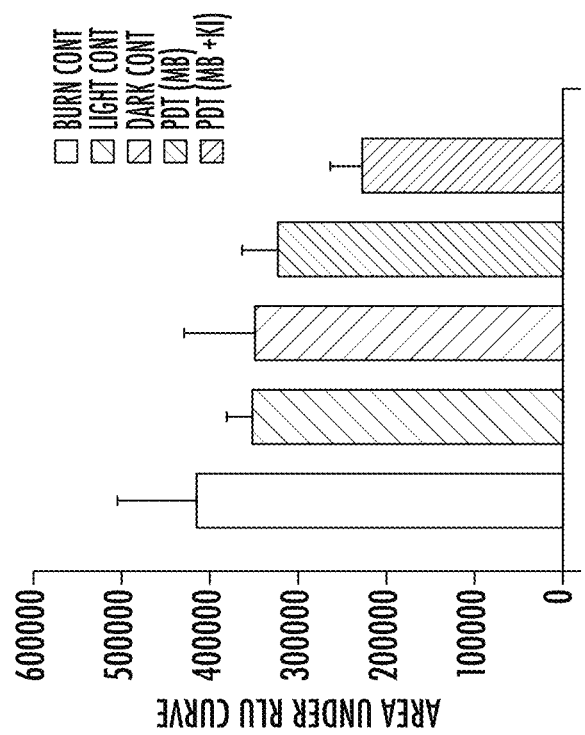
Figure 19F:
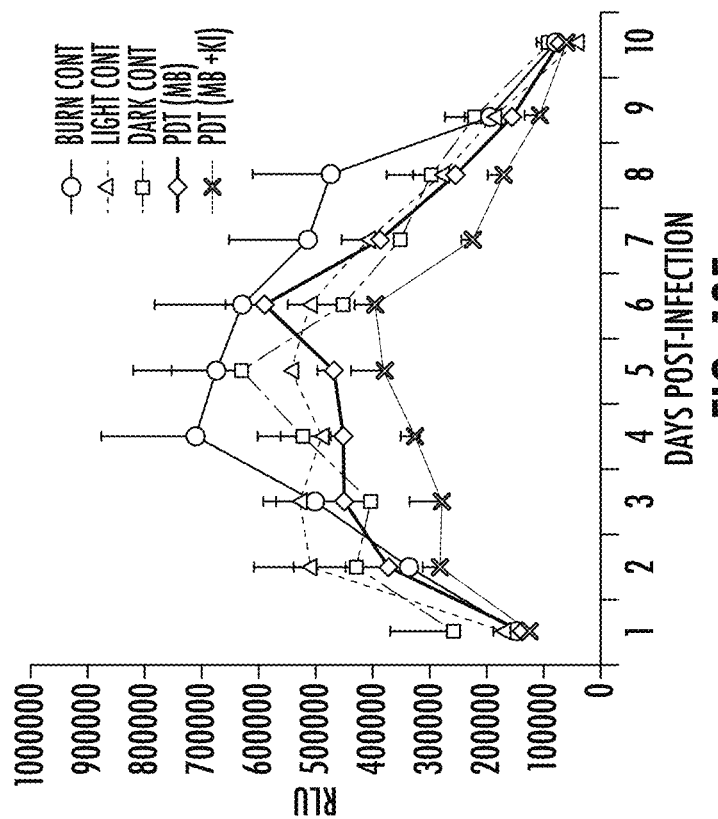

FIGS. 19A, 19B, 19C, 19D, 19E, 19F, 19G illustrate the results of the follow-up monitoring of the bioluminescence images (time courses over 5 days) after the PDI in representative mice from all groups. Consistent differences were observed in bacterial re-growth between PDI performed by using MB+KI (FIG. 19A) and the other groups (FIGS. 19B, 19C, 19D, 19E). In the first case the bacterial re-growth was minimal in that the presence of KI increased the efficacy of PDT at the first treatment to produce sufficient bacterial killing to reduce the recurrence observed during the days post infections, when PDI mediated with the MB alone was not effective to prevent recurrence. The time courses (from day 0 to day 10) of the mean bacterial bioluminescence signal of infected wounds in the different groups of mice are shown in FIG. 19F. The areas under the curves (FIG. 19(i) were compared and PDI potentiated with the mix of MB and KI (group E) was significantly lower than all other groups.

In yet another related embodiment, the experiments described in Example 2 were extended to in vivo studies. Here, thirty minutes after application of the bacteria to the abrasions, The infected abrasion was treated with 200 µM of LC16, with and without the addition of 10 mM of KI and excited with UVA light up to 20 $J/cm^2$ while the control groups were dark controls with the same amount of LC16+KI and light alone control received INA light to 20 $J/cm^2$. The results are shown in FIGS. 20A, 20AB, 20C, 20D, from which it can be seen that a complete elimination of the bioluminescence signal was observed after a UVA dose of 20 $J/cm^2$ was delivered in the presence of LC16+K1. However the LC16+UVA group without added KI still had bioluminescence signals remaining in the wound. Both light and dark controls had no measurable diminution in bioluminescence signal during the course of the experiment.

The results of the experiment using white light to excite the fullerene/iodide combination are shown in FIGS. 21A, 21B, 21C, 21D. The loss of bioluminescence signal was slightly less pronounced after excitation with 120 J/cm2 than it was with 20 J/cm2 UVA light. Nevertheless the addition of iodide also gave a much better bacterial killing when LC16 was excited by white light.

Figure 22B:
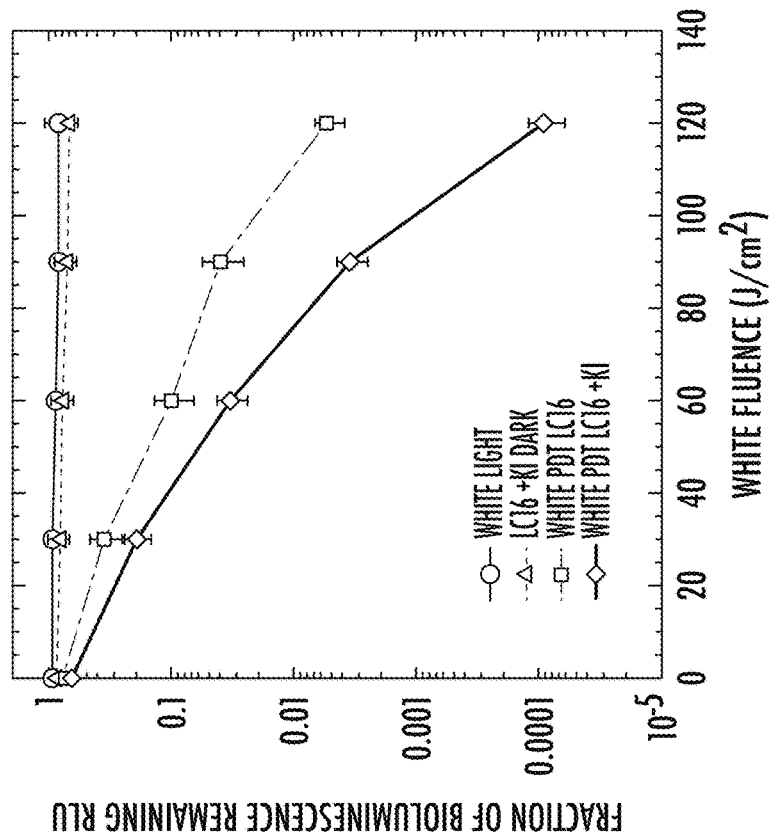
FIGS. 22A and 22B display the light-dose-response curves of the fraction remaining of the normalized bioluminescence signals calculated from the different groups of tissue in vivo.
Figure 22A:
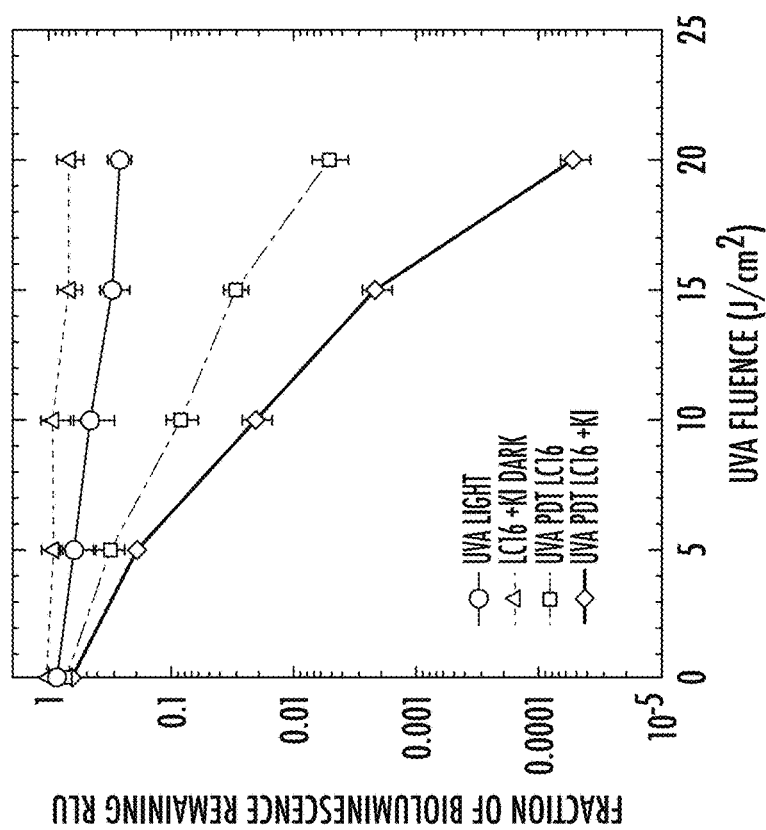

FIGS. 22A and 22B show the light-dose-response curves of the fraction remaining of the normalized bioluminescence signals calculated from the different mouse groups. When UVA was used for excitation of LC16+KI it gave a reduction of over 4-logs while LC16+UVA alone (no K1) gave a reduction of only 2-log of the bioluminescence RLU ($p<0.001$). No significant reduction was seen for either dark or light control. PDT mediated white light excitation of LC16+KI induced a reduction of ca. 4-log in RLU, while LC16 alone+white light gave a reduction of only 2-log of the bioluminescence RLU ($p<0.001$).

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and not all, features of the invention, A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown. The invention as recited in the appended claims is intended to be assessed in light of the disclosure as a whole.

What is claimed is:

1. A method for photodynamic inactivation of target bacteria, the method comprising:
    intermixing first and second compositions of matter to form a mixture of said first and second compositions of matter;
    after said intermixing, treating said target bacteria to form a first amount of treated bacteria by establishing contact between first and second compositions of matter and said target bacteria,
    wherein:
        the first composition of matter comprises a single-component photosensitizer (PS) having a first efficiency in mediating said inactivation on its own in absence of the second composition of matter, said first composition of matter including one of dimethyl-methylene blue, Nile blue derivative material, and titania, and
        the second composition of matter has no efficiency in mediating said inactivation on its own in absence of the first composition of matter wherein said second composition of matter includes at least one of a nitrite salt of an alkaline metal, a thiocyanate salt of an alkaline metal, a selenocyanate salt of an alkaline metal, and a bromide salt of an alkaline metal;
    for a pre-determined duration of time, irradiating said first amount of treated bacteria with light having a wavelength to reduce the first amount of treated bacteria, wherein said wavelength is chosen to trigger photodynamic inactivation of bacteria when said target bacteria is treated with only the single-component PS.

2. A method according to claim 1 wherein said intermixing includes intermixing a first solution of said first composition of matter and a second solution of said second composition of matter.

3. A method according to claim 1,
wherein said irradiating includes reducing the first amount with second efficiency, the second efficiency being equal to M;
wherein M>N; and
wherein N is equal to said first efficiency.

4. A method according to claim 3, wherein M/N is at least 10.

5. A method according to claim 3, wherein M/N is at least 100.

6. A method according to claim 3, wherein M/N is at least 1,000.

7. A method according to claim 1, wherein said irradiating includes transmitting said light along a body of a catheter.

8. A method according to claim 1, wherein said irradiating includes transmitting said light in an optical waveguide disposed within a wall of a catheter to said treated bacteria that is located near a distal portion of said catheter.

* * * * *

UNITED STATES PATENT AND TRADEMARK OFFICE
CERTIFICATE OF CORRECTION

PATENT NO. : 10,780,294 B2
APPLICATION NO. : 15/528015
DATED : September 22, 2020
INVENTOR(S) : Daniela Vecchio et al.

It is certified that error appears in the above-identified patent and that said Letters Patent is hereby corrected as shown below:

In the Specification

Column 3, Line 8, "ma" should be --mammalian--.

Column 3, Line 54, "of" should be --or--.

Column 4, Line 9, "PDT" should be --PDI--.

Column 5, Table 1, Line 15, "Nap" should be --Nal--.

Column 8, Line 56, "Nivea" should be --Niwa--.

Column 11, Line 30, "mM" should be --min--.

Column 17, Line 31, "tight" should be --light--.

Column 19, Line 11, "INA" should be --UVA--.

Signed and Sealed this
Tenth Day of November, 2020

Andrei Iancu
*Director of the United States Patent and Trademark Office*